(12) United States Patent
Worrell et al.

(10) Patent No.: US 11,134,968 B2
(45) Date of Patent: Oct. 5, 2021

(54) SURGICAL JAW COUPLING METHODS AND DEVICES

(71) Applicant: Ethicon Endo-Surgery, LLC, Guaynabo, PR (US)

(72) Inventors: Barry C. Worrell, Dayton, OH (US); Kris Kallenberger, Cincinnati, OH (US); Randolph C. Stewart, Cincinnati, OH (US); Jason R. Lesko, Cincinnati, OH (US); William D. Shaw, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 815 days.

(21) Appl. No.: 14/659,107

(22) Filed: Mar. 16, 2015

(65) Prior Publication Data

US 2016/0270807 A1 Sep. 22, 2016

(51) Int. Cl.
*A61B 17/28* (2006.01)
*A61B 18/14* (2006.01)
(Continued)

(52) U.S. Cl.
CPC ........ *A61B 17/2816* (2013.01); *A61B 17/282* (2013.01); *A61B 18/1445* (2013.01);
(Continued)

(58) Field of Classification Search
CPC .............. A61B 17/2816; A61B 17/282; A61B 18/1445; A61B 2090/032;
(Continued)

(56) References Cited

U.S. PATENT DOCUMENTS 5,632,432 A 5/1997 Schulze et al.
5,700,276 A * 12/1997 Benecke ............ A61B 17/1608
606/206

(Continued)

FOREIGN PATENT DOCUMENTS

EP 0178941 A2 4/1985

OTHER PUBLICATIONS

International Search Report and Written Opinion for Application No. PCT/US2016/20074 dated Jun. 6, 2016.

*Primary Examiner* — Jing Rui Ou
(74) *Attorney, Agent, or Firm* — Mintz Levin Cohn Ferris Glovsky and Popeo, P.C.

(57) ABSTRACT

A surgical end effector is provided having upper and lower jaws pivotally coupled to one another by at least one connecting member that is configured to allow a gap between the jaws to be set at a desired height. In one embodiment, the connecting member can be pivotably coupled to the upper jaw and fixed within a slot in the lower jaw. The connecting member can be fixed within the slot in one of multiple positions so as to position first and second tissue contacting surfaces of the upper and lower jaws at a predetermined distance from one another when the first and second jaws are in the closed position. The connecting member can include a pin formed thereon that extends into a bore formed in the upper jaw. Alternatively, the upper jaw can include a pin formed thereon that extends into a bore formed in the connecting member.

20 Claims, 19 Drawing Sheets

(51) Int. Cl.
 *A61B 90/00* (2016.01)
 *A61B 17/00* (2006.01)
 *A61B 17/29* (2006.01)

(52) U.S. Cl.
 CPC ............... *A61B 2017/00526* (2013.01); *A61B 2017/2936* (2013.01); *A61B 2017/2939* (2013.01); *A61B 2018/1455* (2013.01); *A61B 2090/032* (2016.02)

(58) Field of Classification Search
 CPC .. A61B 2017/00526; A61B 2017/2936; A61B 2017/2939; A61B 2018/1455
 See application file for complete search history.

(56) References Cited

U.S. PATENT DOCUMENTS

| | | | | |
|---|---|---|---|---|
| 6,142,957 | A * | 11/2000 | Diamond | A61B 10/0266 600/567 |
| 6,694,848 | B1 * | 2/2004 | Flavigny | B25B 7/10 81/357 |
| 7,211,099 | B2 * | 5/2007 | Lang | A61B 17/1608 606/206 |
| 8,603,133 | B2 * | 12/2013 | Teichtmann | A61B 17/1608 606/205 |
| 2001/0037109 | A1 * | 11/2001 | Yamauchi | A61B 18/1442 606/48 |
| 2003/0114851 | A1 * | 6/2003 | Truckai | A61B 18/1445 606/51 |
| 2003/0135204 | A1 * | 7/2003 | Lee | A61B 17/0469 606/1 |
| 2003/0139757 | A1 * | 7/2003 | Lang | A61B 17/1608 606/174 |
| 2004/0087943 | A1 * | 5/2004 | Dycus | A61B 17/2909 606/51 |
| 2004/0097911 | A1 * | 5/2004 | Murakami | A61B 17/320092 606/27 |
| 2004/0267311 | A1 | 12/2004 | Viola et al. | |
| 2005/0165429 | A1 | 7/2005 | Douglas et al. | |
| 2005/0262974 | A1 * | 12/2005 | Engvall | B25B 7/10 81/413 |
| 2009/0202387 | A1 | 8/2009 | Dlugos, Jr. et al. | |
| 2012/0074200 | A1 | 3/2012 | Schmid et al. | |
| 2012/0078243 | A1 | 3/2012 | Worrell et al. | |
| 2012/0078247 | A1 | 3/2012 | Worrell et al. | |
| 2012/0310240 | A1 * | 12/2012 | Olson | A61B 18/1445 606/46 |
| 2013/0023868 | A1 | 1/2013 | Worrell et al. | |
| 2013/0053831 | A1 * | 2/2013 | Johnson | A61B 17/2909 606/1 |
| 2013/0079762 | A1 * | 3/2013 | Twomey | A61B 18/1445 606/29 |
| 2013/0218198 | A1 * | 8/2013 | Larson | A61B 17/295 606/206 |
| 2013/0232753 | A1 | 9/2013 | Ackley et al. | |

\* cited by examiner

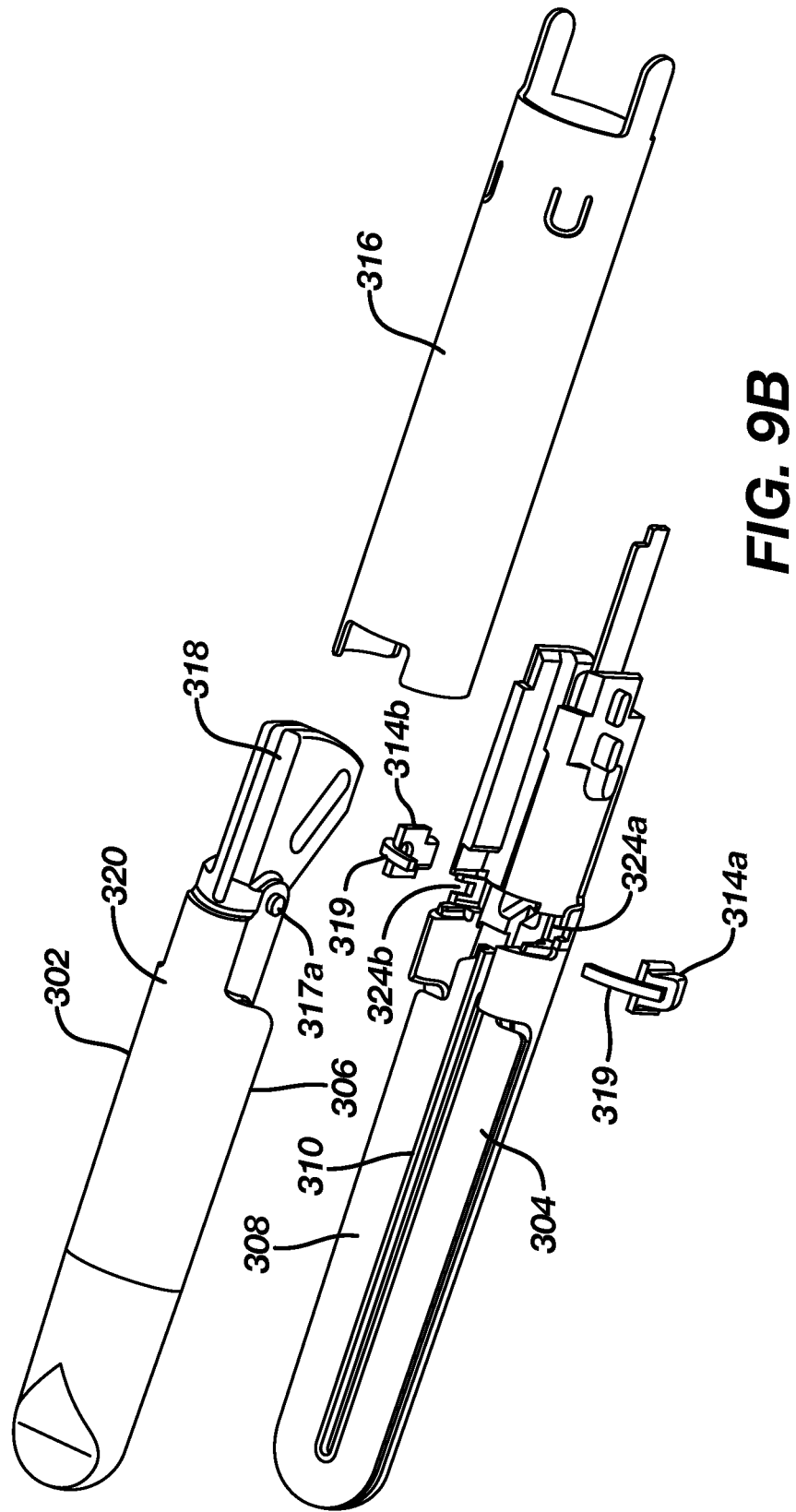

SURGICAL JAW COUPLING METHODS AND DEVICES

FIELD

Methods and devices are provided for assembling a pair of jaws on an end effector of a surgical device.

BACKGROUND

Bipolar electrosurgical instruments apply radiofrequency (RF) energy to a surgical site to cut, ablate, or coagulate tissue. A particular application of these electrosurgical effects is to seal blood vessels or tissue sheets. A typical instrument takes the form of a set of forceps or pair of jaws, with one or more electrodes on both jaws. In an electrosurgical procedure, the jaws are placed in close proximity to each other as the jaws are closed on a target site such that the path of current between the two electrodes passes through tissue within the target site. The mechanical force exerted by the jaws and the electrical current combine to create the desired surgical effect. By controlling the level of mechanical and electrical parameters, such as the pressure applied by the jaws, the gap distance between electrodes, and the voltage, current, frequency, and duration of the electrosurgical energy applied to the tissue, the surgeon can coagulate, cauterize, or seal tissue toward a therapeutic end.

Since bipolar devices pass electrical current between the jaws, the distance or gap between the jaws can be a critical dimension for sealing vessels. Current manufacturing processes can require a series of steps with tightly controlled and time consuming processes to achieve proper jaw alignment and reliable and consistent gap separation between electrodes. Moreover, additional steps are often undertaken to control other parameters associated with the rotational movement about the hinge connecting the jaws, e.g., friction, torque, etc. Controlling parameters such as jaw gap during manufacturing of an end effector is typically an expensive, time- and labor-consuming process.

Accordingly, there remains a need for improved methods and devices for manufacturing an end effector of a surgical instrument.

SUMMARY

Surgical devices and methods for manufacturing devices are provided for allowing a gap between upper and lower jaws of an end effector to be selectively set at a desired distance. In one embodiment, a surgical end effector is provided and includes first and second jaws pivotally coupled to one another, and a connecting member pivotally coupled to the first jaw and disposed within a slot formed in the second jaw. Each jaw can have a tissue contacting surface, and the first and second jaws can be movable between an open position in which the tissue contacting surfaces are spaced apart and a closed position in which the tissue contacting surfaces are configured to engage tissue therebetween. The connecting member can be fixed within the slot at one of a plurality of positions so as to position the first and second tissue contacting surfaces at a predetermined distance from one another when the first and second jaws are in the closed position. When fixed, the connecting member can allow pivotal movement of the jaws between the open and closed positions.

The surgical end effector can have a variety of configurations. For example, in some embodiments, the connecting member can include a pin formed thereon that extends into a bore formed in the first jaw. In other embodiments, the first jaw can include a pin formed thereon that extends into a bore formed in the connecting member.

In one embodiment, prior to being fixed to the second jaw, the connecting member can be configured to slide within the slot in a direction substantially perpendicular to a longitudinal axis of the first and second jaws to allow the gap between the jaws to be adjusted.

In one aspect, the connecting member can be a first connecting member, the slot can be a first slot, and the device can further include a second connecting member pivotally coupled to the first jaw and disposed within a second slot formed in the second jaw. The connecting member can be fixed within the second slot at one of a plurality of positions so as to position the first and second tissue contacting surfaces at a predetermined distance from one another when the first and second jaws are in the closed position. The first and second connecting members can allow pivotal movement of the jaws between the open and closed positions. The first and second slots can be formed in opposite sides of the second jaw. In another embodiment, a bridge can extend between the first and second connecting members.

The first and second jaws can be coupled in various configurations with respect to one another. For example, in one embodiment, the second jaw can be a stationary jaw and the first jaw can be a movable jaw that is configured to pivot relative to the second jaw. In other aspects, both jaws can be pivotally movable about a pivot joint.

Methods for manufacturing an end effector are also provided. In one embodiment, a method can include positioning a tissue contacting surface of a first jaw in facing relation with a tissue contacting surface of a second jaw, and coupling an connecting member to each of the first and second jaws, and adjusting a gap between the tissue contact surfaces of the first and second jaws. The connecting member can slide within a slot in the second jaw during adjustment of the gap. The method can also include fixedly mating the connecting member to the second jaw to prevent sliding of the connecting member within the slot and to thereby set the gap between the tissue contacting surfaces of the first and second jaws. The connecting member can allow the first and second jaws to pivotally move between open and closed positions when the connecting member is fixedly mated to the second jaw The method can vary in a number of ways. For example, in one aspect, the connecting member can be a first connecting member that is coupled to a first side of each of the first and second jaws, and the method further comprises coupling a second connecting member to a second side, opposite to the first side, of each of the first and second jaws, and fixedly mating the second connecting member to the second jaw to prevent sliding of the second connecting member within the slot and to thereby set the gap between the tissue contacting surfaces of the first and second jaws. In another embodiment, coupling the connecting member to each of the first and second jaws can include inserting a pin formed on the first jaw into a bore formed in the connecting member, and sliding the connecting member into a slot formed in the second jaw. Alternatively, coupling the connecting member to each of the first and second jaws can include inserting a pin formed on the connecting member into a bore formed in the first jaw, and sliding the connecting member into a slot formed in the second jaw.

In other aspects, coupling the connecting member to the first and second jaws can include coupling a first end of the connecting member to a first side of each of the first and second jaws, and coupling a second end of the connecting member to a second side of the first and second jaws that is opposite to the first side, wherein a bridge extends between the first and second ends. In other aspects, the method can include inserting a spacer between the tissue contacting surfaces of the first and second jaws to adjust a vertical position of the connecting member within the slot.

The connecting member can be fixedly mated to the second jaw in a variety of ways. For example, the connecting member can be fixedly mated to the second jaw by at least one of welding, application of an adhesive, or application of thermoplastic overmold. When the connecting member is fixed to the second jaw, the tissue contacting surfaces of the first and second jaws can be maintained in a substantially parallel orientation relative to one another. In other aspects, the connecting member can be temporarily and reversibly prevented from sliding within the slot prior to positioning the tissue contacting surfaces of the first and second jaws in facing relation with each other.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 9B is a perspective exploded view of the end effector of FIG. 9A;

DETAILED DESCRIPTION

Figure 1:
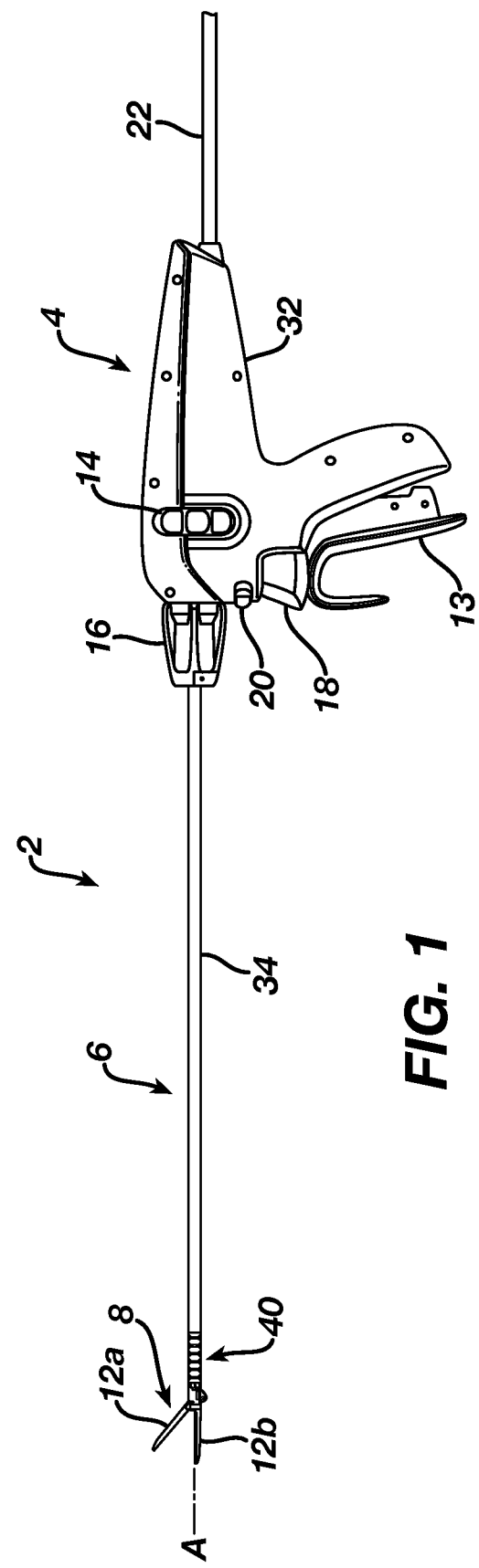
FIG. 1 is a side view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for manufacturing an end effector of a surgical device are provided. In particular, various techniques are provided for allowing a surgical end effector to be manufactured such that a predetermined gap between tissue contacting surfaces of opposed jaws of the end effector can adjusted and fixed during manufacturing in a simple and effective manner.

In general, a surgical end effector is provided that has upper and lower jaws having first and second tissue contacting surfaces. The end effector also includes a hinge or connecting member that can be pivotally coupled to one of the upper and lower jaws, e.g., the upper jaw, and that can be configured to be disposed within a slot formed in the other jaw, e.g., the lower jaw, such that the connecting member can slide within the slot in a direction substantially perpendicular to a longitudinal axis of the jaws. When mated to the jaws, the connecting member can slide within the slot to allow a distance between the tissue contacting surfaces of the jaws to be adjusted. After a predetermined distance or gap is achieved, the connecting member can be fixed within the slot so as to fix the tissue contacting surfaces at the predetermined distance. When the connecting member is fixed to the lower jaw, the upper jaw can pivot relative to the connecting member. Thus, the jaws can move between an open position in which the tissue contacting surfaces of the jaws are spaced apart, and a closed position in which the tissue contacting surfaces are configured to engage tissue therebetween. The predetermined gap will be maintained between the jaws when the jaws are in the closed position. The sliding connection advantageously allows the gap between the jaws to be set within tight tolerances to a desired height or distance Such a configuration provides for a simple and accurate technique for manufacturing opposed jaws for use on a surgical device. The techniques disclosed herein can be particularly useful with bipolar jaws, as the gap between the jaws must be extremely accurate to create the desired surgical effects. For example, a conventional bipolar surgical instrument may have a gap of 0.002 and 0.008 inches between the tissue engaging surfaces of the first and second jaw. However, the methods and devices disclosed herein can be used in conjunction with opposed jaws of an end effector on a variety of other surgical devices.

Figure 2:
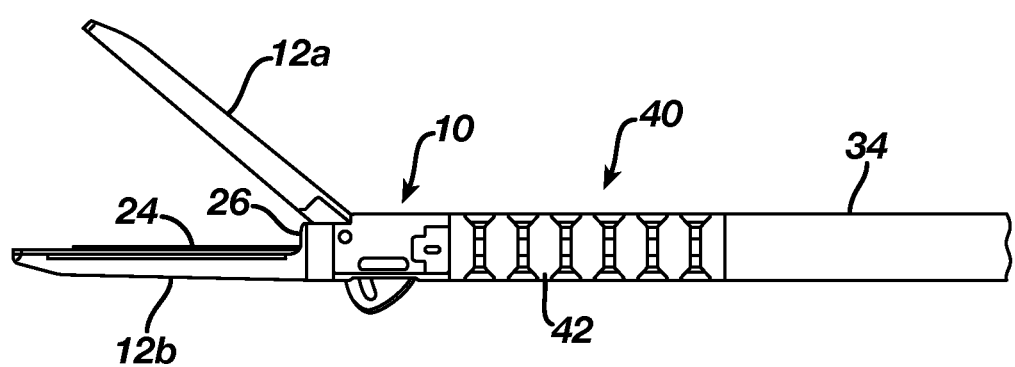
FIG. 2 is a side view of a distal portion of the surgical device of FIG. 1.
Figure 3:
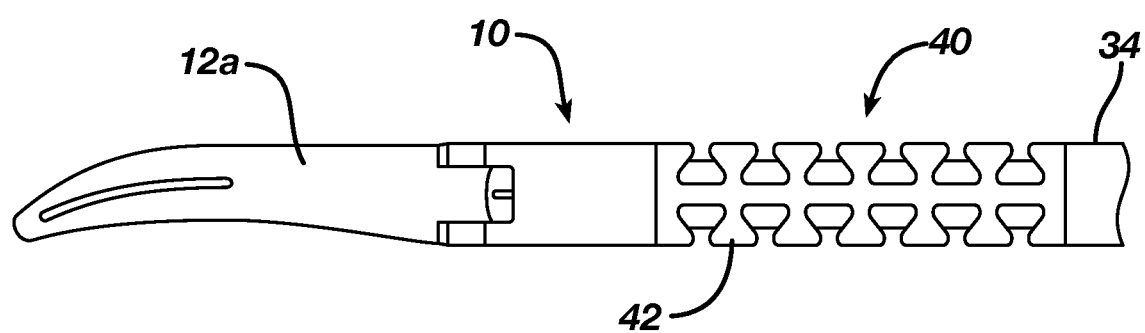
FIG. 3 is another side view of a distal portion of the surgical device of FIG. 1.

FIGS. 1-3 illustrate one embodiment of a surgical device 2 having a proximal handle portion 4 with a shaft assembly 6 extending distally therefrom, and a working element, referred to herein as an end effector 8, that is coupled to a distal end of the shaft assembly 6. The end effector 8 can be coupled to the shaft assembly 6 at a pivot joint 10. The end effector 8 can have a variety of sizes, shapes, and configurations. As shown in FIGS. 1-3, the end effector 8 is disposed at a distal end of the surgical device 2 and has first and second opposed jaws 12a, 12b. The end effector 8 in the illustrated embodiment is in the form of a tissue grasper having a pair of opposed upper and lower jaw 12a, 12b configured to move between open and closed positions. The first top or upper jaw 12a and the second bottom or lower jaw 12b can be pivotally connected together at the pivot joint 10. One or both of the jaws 12a, 12b can include electrodes 24, which can be configured to contact tissue positioned between the jaws 12a, 12b and to apply energy thereto. The electrodes 24 are arranged longitudinally along the lower jaw 12b in the illustrated embodiment, but the electrodes 24 can be arranged in any of a variety of ways on the upper jaw 12a and/or the lower jaw 12b.

It should be appreciated that the surgical device 2 having the handle portion 4 is described herein by way of example only, and that the device need not include a handle. The embodiments disclosed herein can be used in a robotic system in which the shaft assembly and the end effector can be coupled to a robotic arm that is manipulated by a robotic control system. A person skilled in the art will also appreciate that the embodiments disclosed herein can be used in connection with any surgical end effector, and are not intended to be limited to an end effector having jaws. Other exemplary end effectors include, e.g., scissors, a babcock, a retractor, etc.

The handle portion 4 can have a variety of sizes, shapes, and configurations. For example, as shown in FIG. 1, the handle portion 4 can include a main housing 32, which can house a variety of elements therein and can have some elements accessible outside thereof, such as various actuators configured to effect operation of the surgical device. For example, in the illustrated embodiment, the main housing 32 can house a first actuator 13, a second actuator 14, a third actuator 16, a fourth actuator 18, and a fifth actuator 20 of the handle portion 4.

The first actuator 13 can be configured to effect opening and closing of the opposed jaws 12a, 12b, e.g., movement of the jaws 12a, 12b toward and away from one another. The jaws 12a, 12b are shown in the open position in FIGS. 1 and 2 and in a closed position in FIG. 3. In the illustrated embodiment, the upper jaw 12a can be configured to move relative to the lower jaw 12b, which can remain stationary relative to the shaft assembly 6. In other embodiments, the bottom jaw can be configured to move relative to the upper jaw which can remain stationary, or both the upper and lower jaws can move relative to one another.

The second actuator 14 can be configured to effect articulation of the end effector 8, e.g., movement of both jaws 12a, 12b in a same direction relative to a longitudinal axis A of the shaft assembly 6. The articulation can be independent of the opening and closing of the jaws 12a, 12b, which can occur with the end effector in any articulated position. The end effector 8 is shown in an unarticulated position, e.g., at a zero angle relative to the longitudinal axis A, in FIGS. 1-3.

The third actuator 16 can be configured to rotate the shaft assembly 6 with the end effector 8 about the longitudinal axis A of the shaft assembly 6. The fourth actuator 18 can be configured to fire the device, e.g., by causing a cutting element 26 (e.g., a knife, a blade, etc.) to translate through the end effector 8.

As in this illustrated embodiment, the surgical device 2 can be powered and it can be configured as an electrosurgical tool that applies energy to tissue, such as radiofrequency (RF) energy. The handle portion 4 can have a power cord 22 extending proximally therefrom that can be configured to supply electrical power to the device 2, such as by connecting to a generator, by plugging into an electrical outlet, etc. The fifth actuator 20 can be configured to turn on and off the application of the energy, which can be delivered to tissue via the electrodes 24.

As mentioned above, the handle portion 4 is described by way of example only. The surgical device described herein can include a different handle or a control mechanism other than a handle, as the described techniques are not limited to a specific mechanism used to operate the device.

The shaft assembly 6 can have a variety of sizes, shapes, and configurations. The shaft assembly 6 can have any longitudinal length, and in an exemplary embodiment it has a length that allows the handle portion 4 to be manipulated outside a patient's body while the shaft assembly 6 extends through an opening in the body with the end effector 8 disposed within a body cavity. By way of non-limiting example, the length can be in the range of about 14 cm to 45 cm, e.g., about 35 cm. In this way, the end effector 8 can be easily manipulated when the device 2 is in use during a surgical procedure.

The shaft assembly 6 can have any diameter. For example, the shaft assembly's diameter can be less than or equal to about 15 mm, e.g., less than or equal to about 10 mm, less than or equal to about 7 mm, less than or equal to about 5 mm, etc., which can allow for insertion of the shaft assembly 6 through an minimally invasive access device, such as during a laparoscopic surgical procedure. The end effector 8 mated to the shaft assembly's distal end can have a diameter equal to or less than the shaft assembly's diameter, at least when the jaws 12a, 12b are in the closed position, which can facilitate insertion of the device's distal portion into a patient's body.

As shown in FIGS. 1-3, the shaft assembly 6 of the surgical device 2 can include an elongate shaft portion or elongate shaft 34 and a flexible neck 40 extending between the elongate shaft 34 and a proximal end of the end effector 8. The flexible neck 40 can receive therein actuating members passing therethrough so that operation of the actuating members causes the flexible neck 40 to articulate and to thereby cause the end effector 8 to articulate. Thus, the flexible neck 40 can bend so as to allow articulating movement of the end effector 8 in a direction transverse to the longitudinal axis A of the elongate shaft 34, as discussed in more detail below. The flexible neck 40 can flex in opposite directions (e.g., right and left) with respect to the longitudinal axis of the elongate shaft 34.

The flexible neck 40 can be coupled to the end effector 8 and the elongate shaft 34 in any suitable manner, as embodiments are not limited in this respect. Furthermore, although in the illustrated embodiment the flexible neck 40 is coupled distal of and adjacent to the elongate shaft 34, it should be appreciated that the flexible neck 40 can be positioned more proximally along the shaft assembly. It should be appreciated that the surgical device 2 including the flexible neck 40 is shown by way of example only, as the described techniques can be used in any suitable surgical devices, including surgical devices with a non-articulating end effector.

Figure 4A:
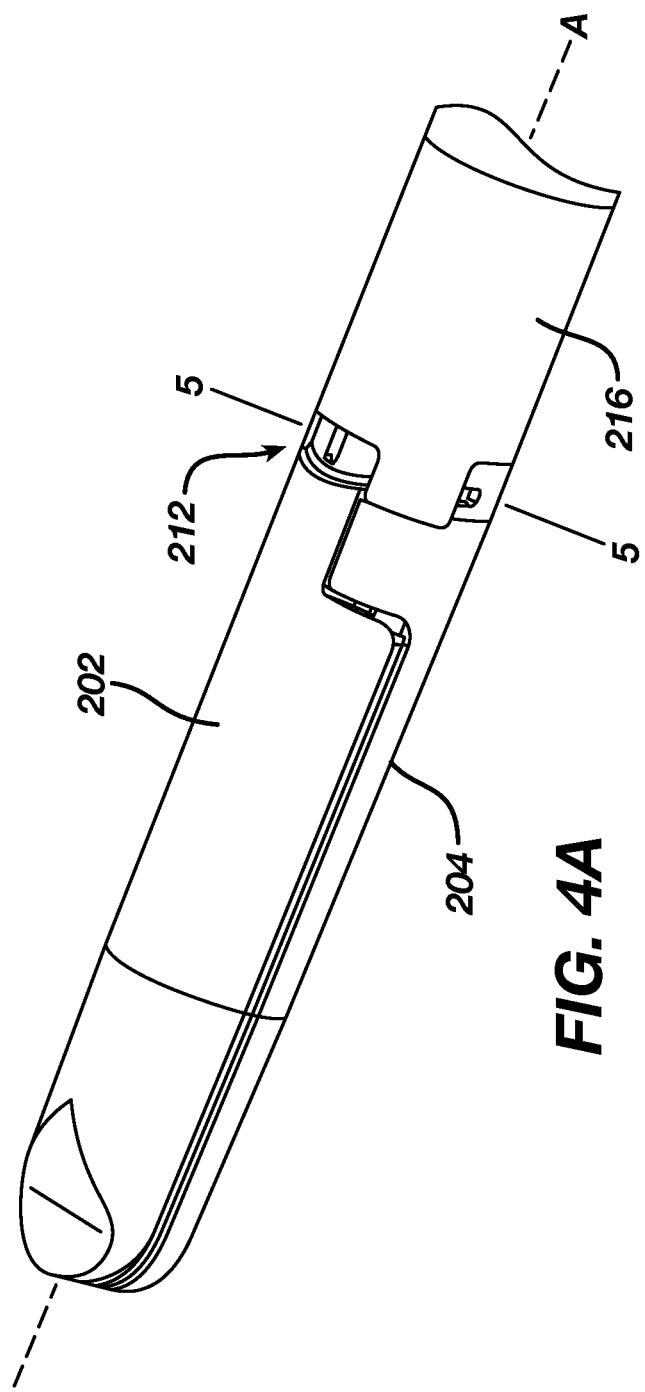
FIG. 4A is a perspective side view of one embodiment of an end effector having at least one connecting member.
Figure 4B:
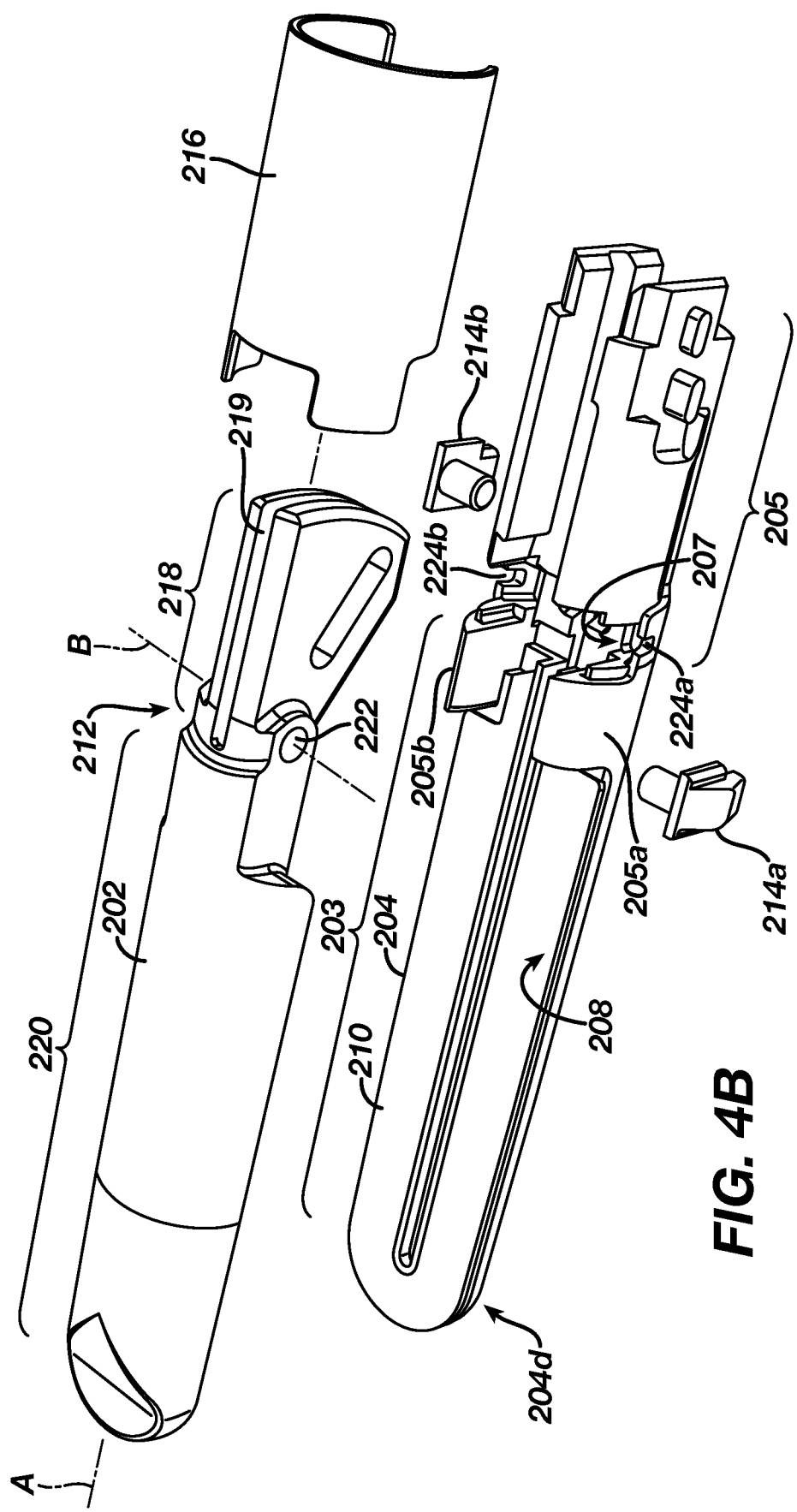
FIG. 4B is a perspective exploded view of the end effector of FIG. 4A.

FIGS. 4A-4D illustrate one embodiment of an end effector 200 manufactured using an adjustable connecting feature for allowing a gap to be set between opposed jaws of the end effector. The end effector 200, which can be similar to end effector 8 (FIGS. 1-3), can be part of any suitable surgical device. The end effector 200, shown in a closed position in FIG. 4A, can include a first upper jaw 202 and a second lower jaw 204 pivotably coupled to one another at a pivot joint 212. The upper and lower jaws 202, 204 have tissue contacting surfaces 206, 208, respectively, that face one another. As shown in FIG. 4B, the end effector 200 also includes first and second connecting members 214a, 214b coupled to opposite sides of the lower jaw 204 at the pivot joint 212. The end effector 200 further includes a housing 216 that encloses a portion of the proximal end of each jaw 202, 204. It should be appreciated that the end effector 200 can include other components coupled thereto and/or extending therethrough that are not shown herein. For example, the end effector can include actuating members such as articulation bands, a cutting element (e.g., a knife), an actuating band for opening and closing the jaws, and one or more conductors extending therethrough. The end effector can also include various elements for coupling the actuating members thereto, moving the upper jaw with respect to the lower jaw, etc.

The connecting members 214a, 214b can be fixed within the opposed slots in the lower jaw 204 in one of multiple positions so as to position the first and second tissue contacting surfaces 206, 208 of the upper and lower jaws 202, 204 at a predetermined distance or gap from one another when the upper and lower jaws 202, 204 jaws are in the closed position, as discussed in more detail below.

In the illustrated exemplary embodiment, at least a portion of the pivot joint 212 is disposed within the arcuate housing 216 coupled to the end effector 200 at a proximal end thereof. It should be appreciated that the housing 216 can have any suitable configuration, as embodiments are not limited in this respect.

One or both of the jaws 202, 204 can include electrodes 210, which can be configured to contact tissue engaged between the jaws 202, 204 and to apply energy thereto. In the illustrated embodiment, the end effector 200 is part of an electrosurgical device in which the electrodes 210 are arranged longitudinally along the lower jaw 204, but the electrodes 210 can be arranged in any of a variety of ways on the upper jaw 202 and/or the lower jaw 204.

The upper jaw 202 can have any suitable configuration. As shown in FIGS. 4A-4D, the upper jaw 202 can include a proximal portion 218 proximal to the pivot joint 212, and an elongate distal portion 220 disposed distally of the pivot joint 212 and having the tissue contacting surface 206 thereon. The distal end of the proximal portion 218 can have a bore or opening formed at least partially therethrough at each side of the upper jaw 202, at opposite sides of a longitudinal axis A of the end effector 200. As shown in FIG. 4B, first and second bores 222a, 222b formed on opposite sides of the upper jaw 202 are disposed along a same axis B that extends transverses, e.g., perpendicular, to the longitudinal axis A of the end effector. In the illustrated embodiment, each of the first and second bores 222a, 222b are configured to receive therein a pin coupled to a respective one of the connecting members 214a, 214b, as discussed in more detail below. The bores 222a, 222b can have a round, oval, or other cross-section, and they can be configured to correspond to a configuration of the pin received therein.

The proximal and distal portions 218, 220 of the upper jaw 202 have a slot 219 extending therethrough that receives a knife. One skilled in the art will appreciate that the upper jaw 202 can have any other suitable features.

The lower jaw 204 can also have any suitable configuration. As shown in FIGS. 4A-4D, the lower jaw 204 can have a proximal portion 205 and a distal portion 203 extending distally therefrom and having the tissue contacting surface 208. The proximal portion 205 of the lower jaw 204 has opposite sidewalls 205a, 205b forming an inner cavity 207 therebetween, as shown in FIG. 4B. The inner cavity 207 can be configured to movably receive therein the proximal portion 218 of the upper jaw 202. The upper jaw 202 is coupled to the lower jaw 204 at the pivot joint 212 such that the upper jaw 202 pivots with respect to the lower jaw 204.

The proximal portion 205 of the lower jaw 204 can include mating features configured to couple suitable actuation elements (e.g., articulation elements, a cutting element, one or more conductors, an actuating band for opening and closing the jaws, etc.) to the end effector 200. The mating features can include pins, protrusions, slots, and any other features.

As shown, the lower jaw 204 can have first and second slots 224a, 224b formed at the opposite sidewalls 205a, 205b thereof. The first and second slots 224a, 224b are configured to slidably receive therein the first and second connecting members 214a, 214b, respectively. When the connecting members 214a, 214b are disposed within the slots and coupled to the upper and lower jaws, the connecting members 214a, 214b allow pivotal movement of the upper and lower jaws 202, 204 between open and closed positions. In the illustrated embodiment, the upper jaw 202 can be coupled to the lower jaw 204 such that the upper jaw 202 pivots with respect to the lower jaw 204 while the lower jaw 204 remains stationary, e.g., relative to an elongate shaft coupled thereto. However, as one skilled in the art will understand, the surgical device can include an end effector having other configurations. For example, in some embodiments, both of the jaws can pivot with respect to one another and relative to an elongate shaft coupled thereto.

Figure 4D:
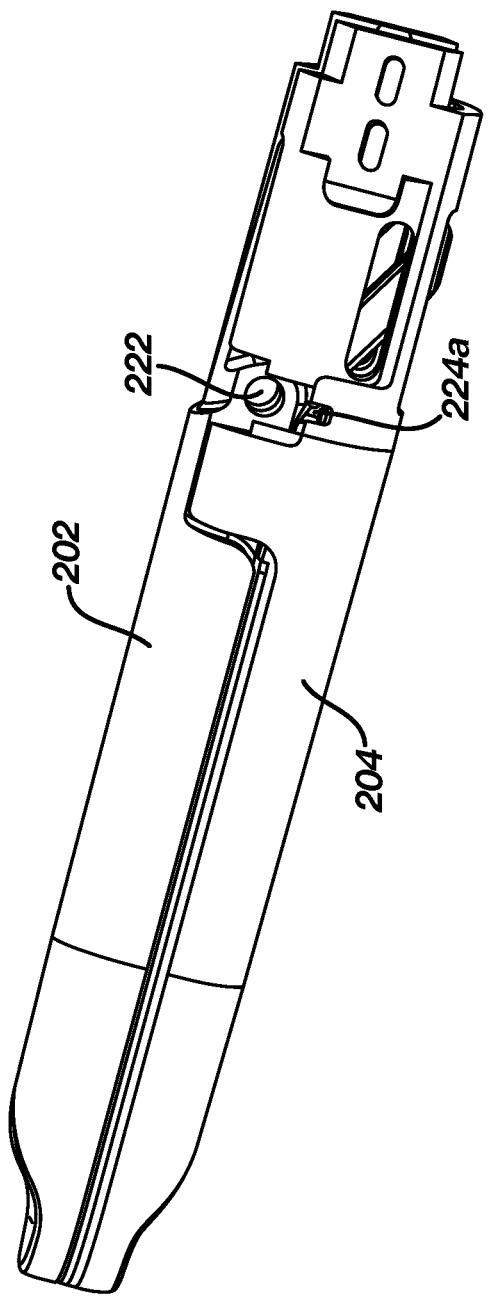
FIG. 4D is another perspective view of the end effector of FIG. 4A, showing a hole in the upper jaw for receiving a pin on a connecting member (not shown)
Figure 5A:
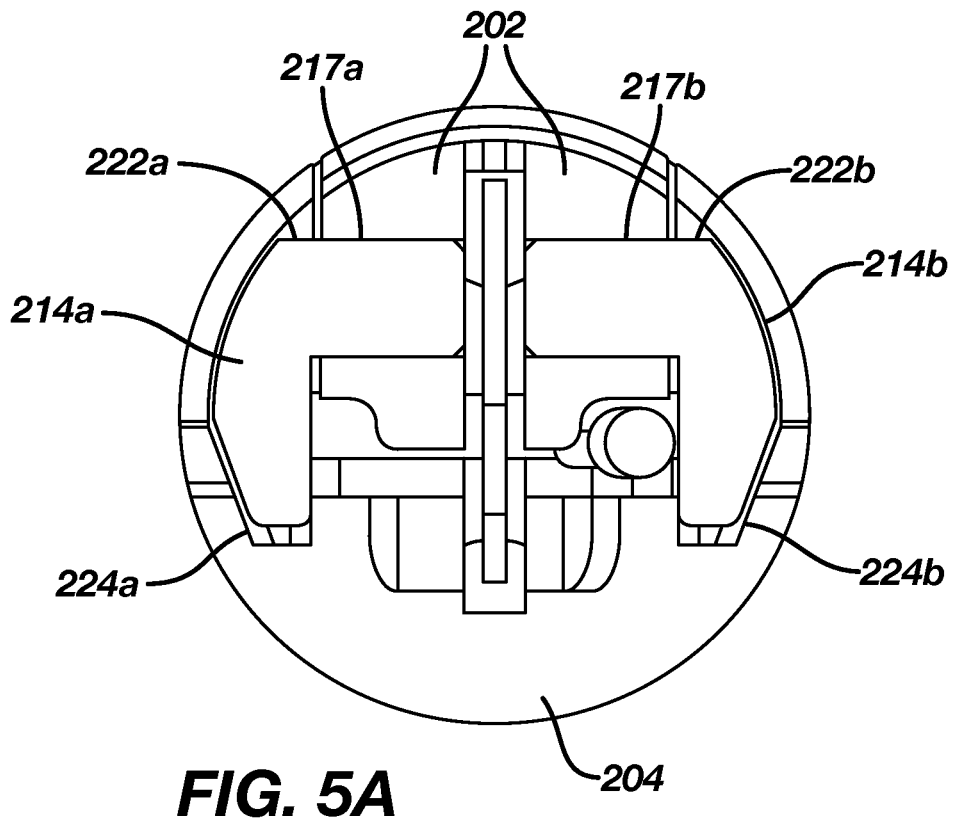
FIG. 5A is a cross-sectional view taken across line 5-5 of the end effector of FIG. 4A.

The first and second slots 224a, 224b in the lower jaw 204 can have a shape and size suited to fit therein the connecting members 214a, 214b, as discussed in more detail below. The first and second slots 224a, 224b can be configured such that the connecting members 214a, 214b can slide within the slots and can then be fixed therein at a desired position. As shown in FIG. 4D, the upper and lower jaws 202, 204 are positioned with respect to one another so that the first bore 222a in the upper law 202 is aligned with the first slot 224a in the lower jaw 204. In this way, when the first connecting member 214a is received within the first slot 224a, a pin 217a of the connecting member 214a is inserted into the first bore 222a, as shown in FIG. 5A. In the same manner, as also shown in FIG. 5A, when the second connecting member 214b is received within the second slot 224b, a pin 217b of the connecting member 214b is inserted into the second bore 222b.

Figure 6C:
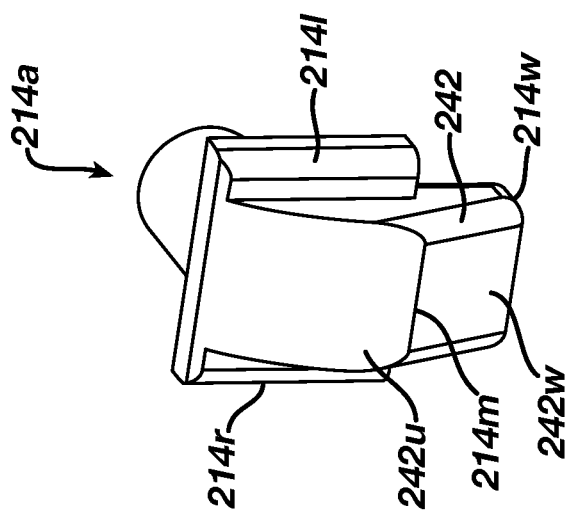
FIG. 6C is another perspective view of the connecting member of FIG. 6A.
Figure 6B:
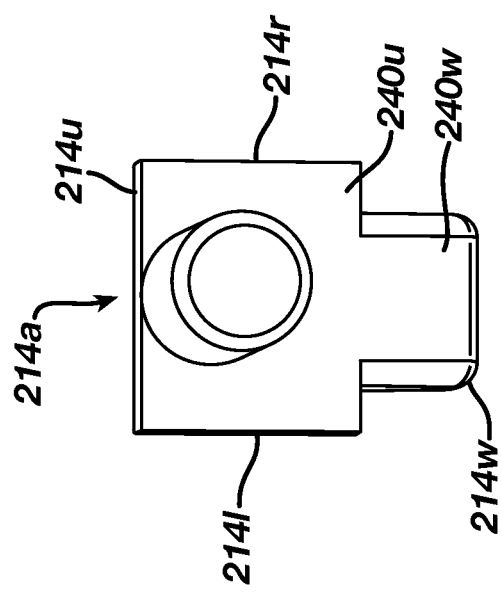
FIG. 6B is another perspective view of the connecting member of FIG. 6A.
Figure 6A:
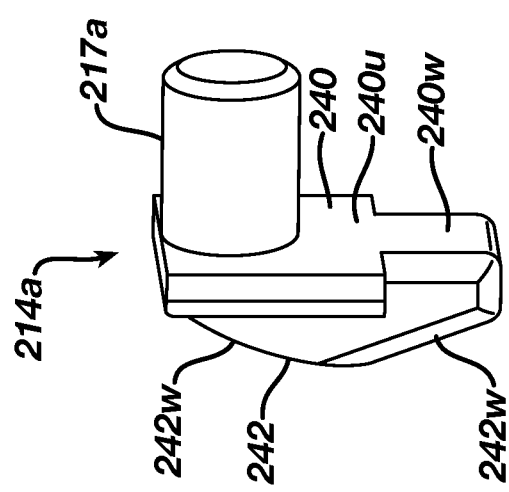
FIG. 6A is a perspective view of a connecting member of the end effector of FIG. 4A.

Each of the connecting members 214a, 214b can vary in a number of ways. FIGS. 6A-6C illustrate connecting member 214a. A person skilled in the art will appreciate that connecting member 214b can be identical to connecting member 214a. The illustrated connecting member 214a is a separate component from the jaws and it is configured to adjust a distance between the upper and lower jaws 202, 204 as measured when the jaws are in a closed position. This facilitates its manufacturing, simplifies the assembly process, and can reduce costs.

As shown in FIGS. 6A and 6C, the connecting member 214a has a substantially planar front wall 240 having a mating portion configured to couple to a bore in the upper jaw 202, and a generally convex back wall 242. As shown, the front wall 240 has a mating portion in the form of a boss or pin 217a extending therefrom. The front wall 240 is generally T-shaped and a lateral width (e.g., from a right side 214r to a left side 214l of the front wall 240) of a horizontal portion of the "T" (an upper portion 240u) is wider than a lateral width of a stem of the "T" (a lower portion 240w), as shown in FIG. 6B.

As shown in FIG. 6C, lateral sides of the curved back wall 242 can be offset at approximately the same distance from right and left 214r, 214l sides of the front wall 240. Thus, a lateral width of the back wall 242 can be less than a lateral width of the front wall 240. The curved back wall 242 can have an upper portion 242u extending outward and a lower portion 242w extending inward and separated from the upper portion 242u by a mid-portion 242m. In other words, the upper portion 242u is angled away from the front wall 240 toward the mid-portion 242m and the lower portion 242w is angled away from the mid-portion 242m toward the front wall 240.

In the illustrated embodiment, the mid-portion 242m can be in the form of an edge disposed between the upper and lower portions 242u, 242w. However, the mid-portion 242m can be curved (e.g., at least partially convex and/or at least partially concave) or it can have any other configuration. In the illustrated embodiment, the mid-portion 242m can be disposed closer to the bottom end 214w of the connecting member 214a than to its top end 214u. However, it should be appreciated that the mid-portion 242m can be disposed approximately mid-way between the top and bottom ends 214u, 214w of the connecting member 214a or at other distances between the top and bottom ends 214u, 214w.

As mentioned above, the top portion 242u of the back wall 242 is slanted and extends from the top end 214u of the connecting member 114 to the mid-portion 242m such that the top portion 242u has a side width that is greater at the mid-portion 242m than at the top end 214u. The side width of the top portion 242u can increase from the top end 214u toward the mid-portion 242m gradually and the top portion 242u can be at least partially convex, as shown in FIGS. 6A and 6C. The convex configuration conforms to a convex shape of an outer wall of the lower jaw. However, in some embodiments, the top portion 242u can be substantially flat. The bottom portion 242w of the back wall 242 can also be slanted and it has a side width that is greater near the mid-portion 242m than at the bottom end 214w of the connecting member 114. The bottom portion 242w of the back wall 242, together with at least part of the bottom portion 240w of the front wall 240 (e.g., at least a part of the stem of the "T") and side surfaces of the connecting member 214a can form a mating surface of the connecting member 214a that engages the inner surface of the slot formed in the lower jaw, as discussed below.

The pin or boss 217a extending from the front wall 240 of the connecting member 214a can have any suitable configuration. The pin 217a extends from an inner side of the front wall 240 referred to as such because this side faces the inner cavity 207 of the lower jaw 204, as discussed in more detail below. As shown in FIGS. 6A and 6B, the pin 217a is disposed near a top end 214u of the connecting member 214a and is located approximately mid-way between left and right sides 214l, 214r of the front wall 240. The pin 217a can be configured to fit within a bore 222a within the upper jaw 202 (FIGS. 4B-4D) and its length, diameter, and shape can thus correspond to those of the bore 222a. The configuration should allow the upper jaw to pivot about the pin. FIG. 5A illustrates that the pins 217a, 217b can be configured to extend through the entire length of the bores 222a, 222b. The pin 217a can be integrally formed with the connecting member 214a or the pin 217a can be fixedly coupled to the front wall 240 in a suitable manner.

The connecting member 214a can be formed as a separate component in any suitable manner. For example, it can be made using injection molding (e.g., metal injection molding) from stainless steel (e.g., 17-4 stainless steel). However, one skilled in the art will understand that the connecting member can be manufactured using any suitable process, from any suitable materials.

Figure 7:
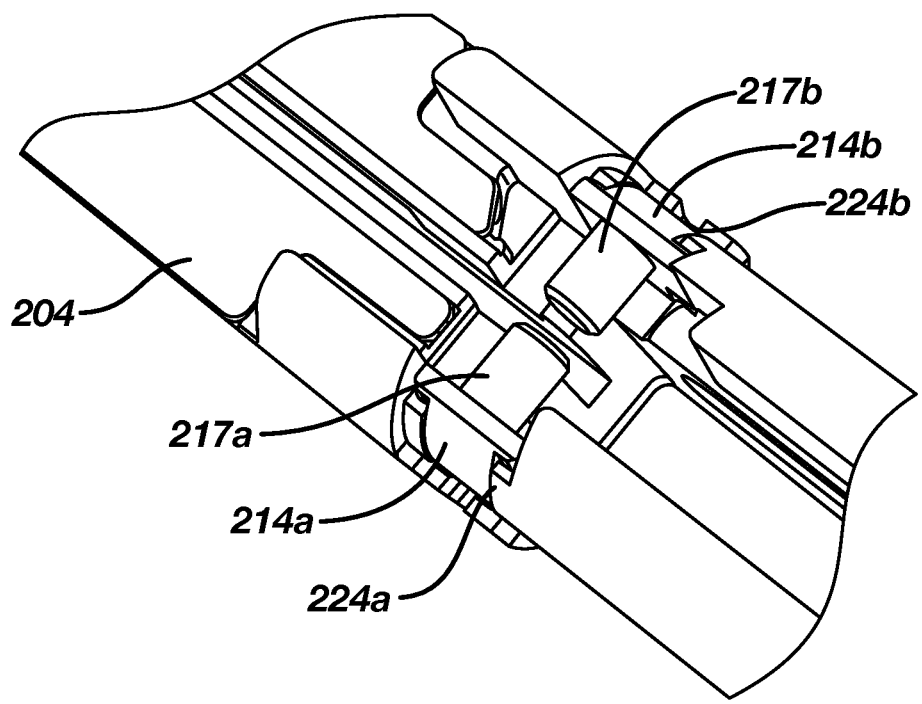
FIG. 7 is a perspective top view of a lower jaw of the end effector of FIG. 4A, showing connecting members seated within opposed slots formed in the lower jaw.
Figure 8A:
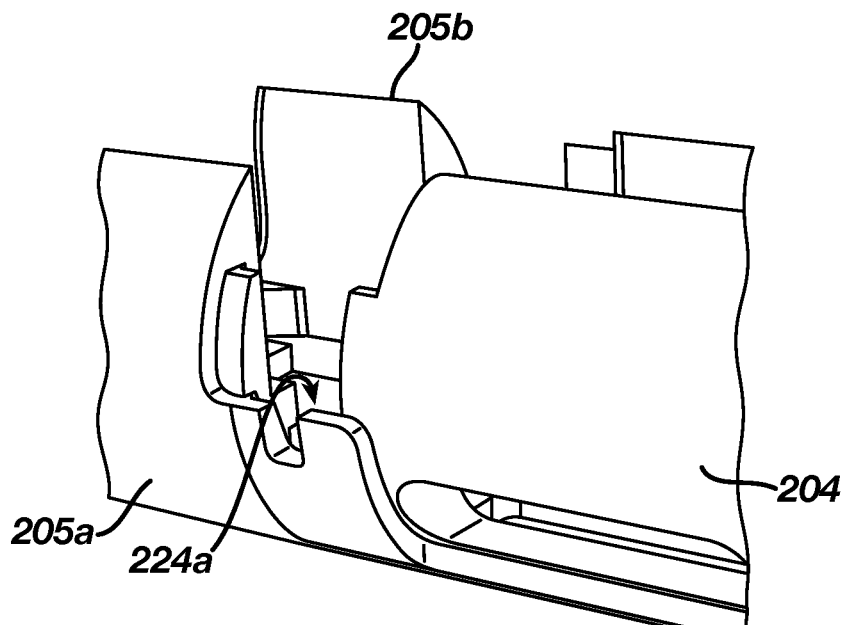
FIG. 8A is a perspective side view of a lower jaw of the end effector of FIG. 4A, showing a slot in the lower jaw.
Figure 8B:
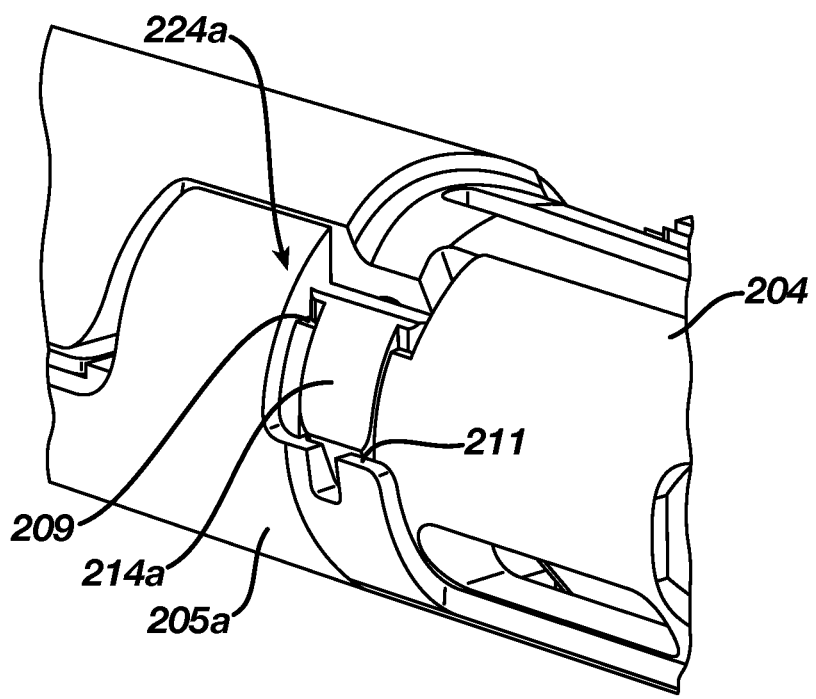
FIG. 8B is a perspective side view of the slot in the lower jaw of FIG. 8A having a connecting member seated therein.

As indicated above, in the illustrated embodiments, each connecting member 214a, 214b is configured to be coupled to the jaws 202, 204 such that the connecting members 214a, 214b set a distance between tissue contacting surfaces 206, 208 of the upper and lower jaws 202, 204. FIG. 7 illustrates connecting member 214a slidably positioned within slot 224a formed in the lower jaw 204, and connecting member 214b slidably positioned within slot 224b formed in the lower jaw 204. With reference to FIGS. 8A-8E, which show one or both connecting members, the slots 224a, 224b can be formed such that at least the bottom portion is configured to seat therein the connecting member 214a, 214b. As shown in FIG. 8B, the slot 224a can be recessed from an outer surface of the sidewall 205a of the lower jaw 204 such that the inner surface of the slot 224a seating the connecting member is offset from the outer surface of the sidewall 205a. As also shown in FIG. 8B, the connecting member 214a can be seated within the slot 224a such that the front wall 240 (FIGS. 6A-6C) of the connecting member faces the inner cavity in the lower jaw 204 and is therefore not visible, whereas the back wall 242a is visible and is recessed from the surface of the sidewall 205a. As also shown, the flanges of the bar of the "T" of the front wall 240 are seated inside the slot such that at least a portion thereof protrudes above upper edges 209 of the sidewall 205a having the slot.

Figure 8C:
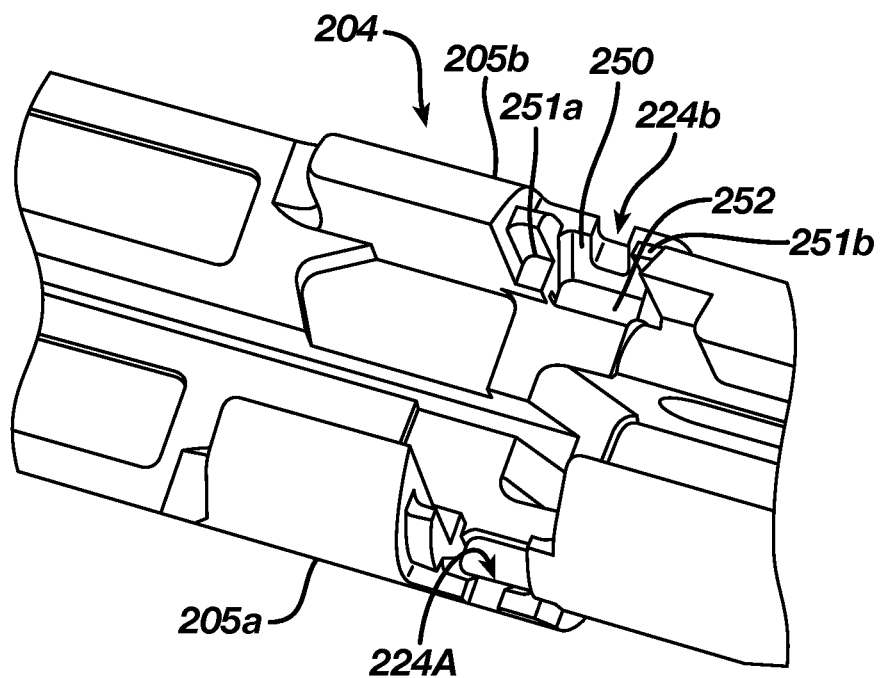
FIG. 8C is a perspective top view of a lower jaw of the end effector of FIG. 4A showing opposed slots formed in the lower jaw.
Figure 8D:
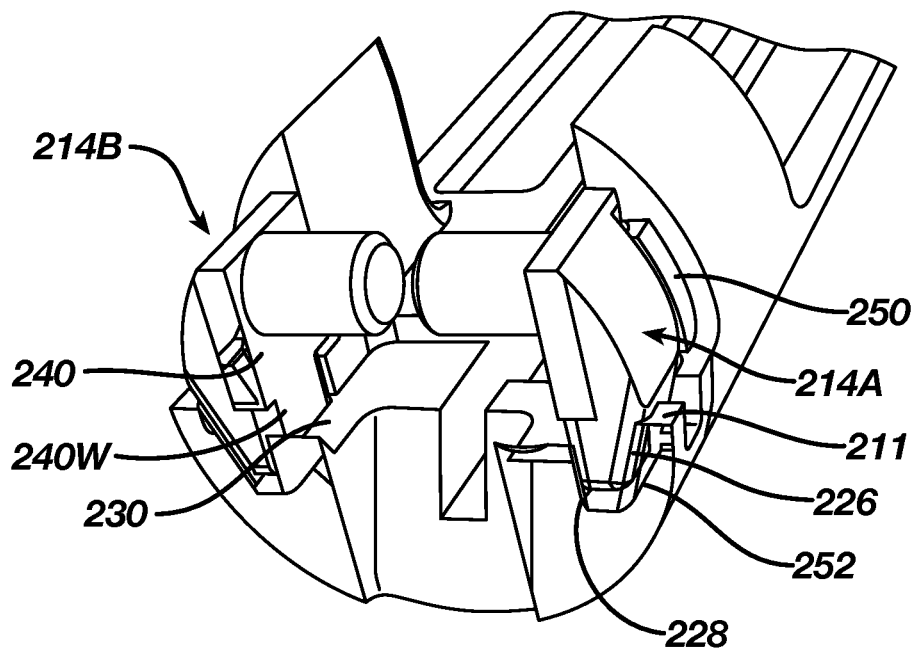
FIG. 8D is a perspective partially transparent cross-sectional top view of a lower jaw of the end effector of FIG. 4A, showing connecting members seated in opposed slots formed in the lower jaw.

In the illustrated embodiment, a configuration of the slots 224a, 224b can be such that the connecting members 214a, 214b can slidably fit within the slots 224a, 224b before they are fixed therein. As shown in FIGS. 8C and 8D, a configuration of the slots 224a, 224b can be at least partially complimentary to the configuration of the connecting members 214a, 214b. For example, as shown in FIGS. 8C and 8D, each of the slots 224a, 224b formed at both sides of the lower jaw 204 has a contour suitable to fit a respective one of the connecting members 214a, 214b. Thus, each of the slots 224a, 224b can have an upper portion 250 generally complimentary to an upper portion of the connecting members 214a, 214b and a lower portion 252 generally complimentary to a lower portion of the connecting members 214a, 214b. Furthermore, as also shown, the slots can have at least partially T-shaped portion to fit at least a portion of the front wall of the connecting members 214a, 214b and the slots 224a, 224b can also have a generally convex portion configured to seat the back wall of the connecting members 214a, 214b.

It should be appreciated that a slot in the lower jaw (or, in some embodiments, an upper jaw) configured to receive the connecting member can have any configuration such that the slot is suitable to receive therein a connecting member of a certain configuration. Furthermore, the slot can be configured such that inner structures of the jaw, including movable and fixed elements, are shielded and thus not affected during the process of permanently fixing the connecting member disposed in the slot to the jaw. For example, the slot can be configured with a staggered offset from internal components of the jaw, or by having an angled and/or convoluted structure separating at least a portion of the connecting member from the internal components of the jaw. In some embodiments, the connecting member and the slot can be configured such that the connecting member fits into the slot like a tongue into a groove. As another non-limiting example, a shiplap coupling can be used. Any other configurations of the connecting member and the slot can be used as well.

Referring back to FIG. 8C, the upper portion 250 of each slot 224a, 224b (as shown in connection with the slot 224b) has lateral cut-outs in the wall of the lower jaw that are configured to seat therein the flanges of the bar of the "T" of the front wall 240 of the connecting member 214a. The external wall of the upper portion 250 also has an opening through which the back wall 242 of the connecting member can be visible, as shown in FIG. 8D.

The lower portion 252 of the slot 224a can be in the form of a pocket having a slanted wall 226 extending from an edge 211 on the outer surface of the sidewall 205a and an opposite substantially planar wall 228. The pocket is configured to seat therein at least a portion of the connecting member, as shown in FIG. 8D for both of the connecting members 214a, 216b. Thus, the slanted wall 226 can be angled toward the longitudinal axis A of the end effector 200 in a manner that is at least partially complementary to the lower portion 242w of the back wall 240 of the connecting member. The opposite wall 228 can extend in a plane substantially perpendicular to the longitudinal axis A of the end effector and can mate with at least a portion of a bottom portion of the front wall 240 of the connecting member. The shape of the sides of the pocket-like lower portion 252 can also be complementary to the side walls of the connecting member 214a, 214b that are disposed between the front and back walls 240, 242.

In some embodiments, prior to positioning the tissue contacting surfaces of the upper and lower jaws 202, 204 in facing relation with each other, the connecting member can be retained within the pocket-like lower portion 252 such that it does not move within the pocket. In some embodiments, additional elements can be used, as discussed below.

As shown in FIGS. 8C and 8D, the side walls of the slot can have different height such that an upper surface 230 of the planar wall 228 can be disposed in a plane below a plane extending through the edge 211. Further, as shown in FIG. 8D, each of the connecting members 214a, 214b can be disposed within the slot such that at least a portion of the lower portion 240w of the front wall 240 of the connecting member protrudes above the inner surface 230 of the lower jaw 204.

Referring back to FIG. 7, the connecting members 214a, 214b can be disposed within the slots 224a, 224b, respectively, such that the pins 217a, 217b disposed thereon face each other and extend along the same axis within the inner cavity 207 of the lower jaw 204, as also shown in FIG. 8D. The pins 217a, 217b are positioned such that a space is formed therebetween so that a cutting member (e.g., a knife) can pass therethrough. The upper jaw 202 (not shown) can be mated to each of the connecting members 214a, 214b by receiving the pin 217a, 217b in the bores 222a, 222b (FIGS. 4A-4D and 5). In this way, the upper and lower jaws 202, 204 are pivotally movable about the pins on the connecting members.

In some embodiments, the connecting members 214a, 214b can be disposed within the slots 224a, 224b such that the connecting members 214a, 214b are prevented from sliding within the slots during certain steps of assembly of the end effector. Furthermore, in some embodiments, an additional component can be used to prevent the connecting members from sliding within the slots before such movement is desired. For example, a tube can be advanced longitudinally along the end effector so as to be positioned over the slot and connecting member to thereby reversibly constrain movement of the connecting member. Any other element(s) can be used for this purpose additionally or alternatively. Such constraints on the movement of the connecting member are reversible such that it can be allowed to move within the slot (e.g., vertically and/or angularly) during subsequent steps of assembly of the end effector.

The connecting members 214a, 214b can be fixed within the slots 224a, 224b at one of a plurality of positions so as to position the first and second tissue contacting surfaces 206, 208 of the upper and lower jaws 202, 204 at a predetermined distance from one another when the upper and lower jaws 202, 204 are in the closed position. For example, sliding movement of the connecting members 214a, 214b toward or into contact with a bottom surface of each slot 224a, 224b will position the tissue contacting surfaces 206, 208 of the jaws 202, 204 closer together or in direct contact with one another. The connecting members 214a, 214b can be configured to slidably move within the slots 224a, 224b in any suitable manner. For example, movement of the upper jaw 202 away from the lower jaw 204 in the illustrated embodiment will cause sliding movement of each of the connecting members 214a, 214b upward within the slot, e.g., in a direction substantially perpendicular to a longitudinal axis of the lower jaw 204. This results from the upper jaw 202 being coupled to the connecting members 214a, 214b at the pins 217a, 217b. In other words, movement of the connecting members 214a, 214b and their respective pins 217a, 217b will push the upper jaw 202 away from the lower jaw 204, thereby increasing the gap between the jaws. A person skilled in the art will appreciate that movement of the connecting members can be caused by movement of the jaws relative to one another, and vice versa. It should also be appreciated that the connecting members 214a, 214b can move within the slots in other ways, different from the direction substantially perpendicular to the longitudinal axis of the jaws. For example, in some embodiments, depending on a configuration of the upper and lower jaws and the way they are configured to pivot with respect to one another, the connecting members 214a, 214b can move within the slots at an angle to the longitudinal axis of the jaws.

When the gap is set at a desired distance, the connecting members 214a, 214b can be fixed, temporarily or permanently, at that location within the slots 224a, 224b. As will be discussed in detail below, fixing can be achieved using various techniques. Once the connecting members 214a, 214b are fixed at a particular position within each slot 224a, 224b, the gap between the tissue contacting surfaces is precisely set and is maintained during use of the device.

In some embodiments, the position of the connecting members within the slots can be adjusted using a shim, spacer, or any other feature. For example, in one embodiment, a spacer can be positioned between the opposed jaws to set a distance or gap between the jaws, and the connecting members can be fixed within the slots when the jaws are closed about the spacer. Thus, as shown by way of example only in FIG. 5B, a shim or spacer 225 is disposed between the tissue contacting surfaces of the upper and lower jaws 202, 204. The jaws 202, 204 are in the closed position, and the connecting members 214a, 214b are disposed within the slots 224a, 224b. The shim will thus set the gap between the jaws, and set the position at which the connecting members 214a, 214b should be fixed so as to maintain the desired gap. It should be appreciated that the shim 225 is shown as a generally rectangular element by way of example only, as the shim 225 can have any suitable configuration. The thickness of the shim, or any other dimension thereof, can be used to set a distance between the upper and lower jaws 202, 204 in the closed position. It should also be appreciated that one or more shims or any other elements can be used. Also, any other suitable features and techniques can be used to adjust a position of the connecting members 214a, 214b within the slots 224a, 224b. In addition, in some embodiments, a technique used can be such that no shim or spacer is retained within the slot in the assembled device.

In the embodiment described above, a mating portion (e.g., a pin or boss) is coupled to a connecting member or hinge coupled to both upper and lower jaws of an end effector so as to set a distance between tissue contacting surfaces thereof. The mating portion can be implemented in other ways. Accordingly, FIGS. 9A-13B illustrate another embodiment of an end effector 300 including a connecting member or hinge that does not include a pin but rather has a bore for receiving such pin. The pin can be coupled to or integrally formed in the upper jaw.

Figure 4C:
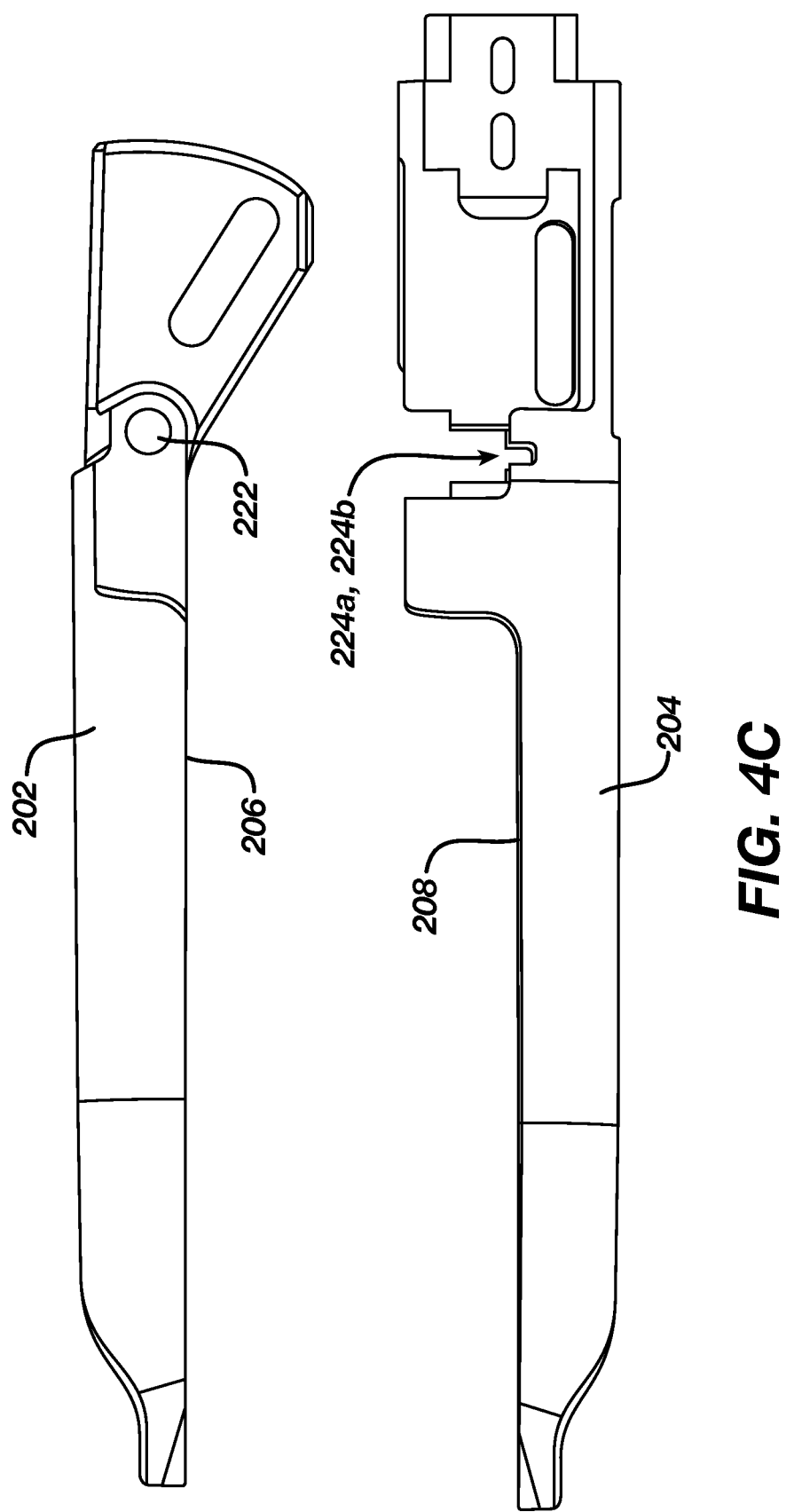
FIG. 4C is another perspective exploded view of a portion of the end effector of FIG. 4A.
Figure 9A:
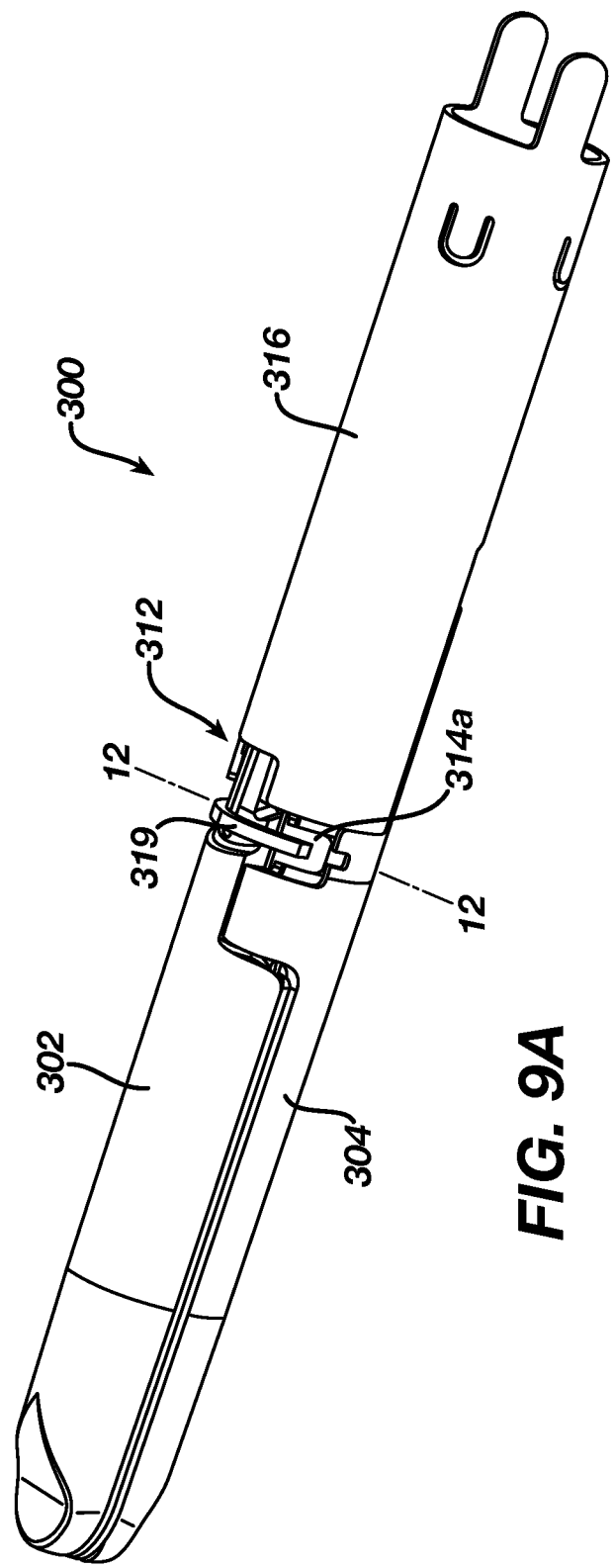
FIG. 9A is a perspective view of another embodiment of an end effector having at least one connecting member.
Figure 9C:
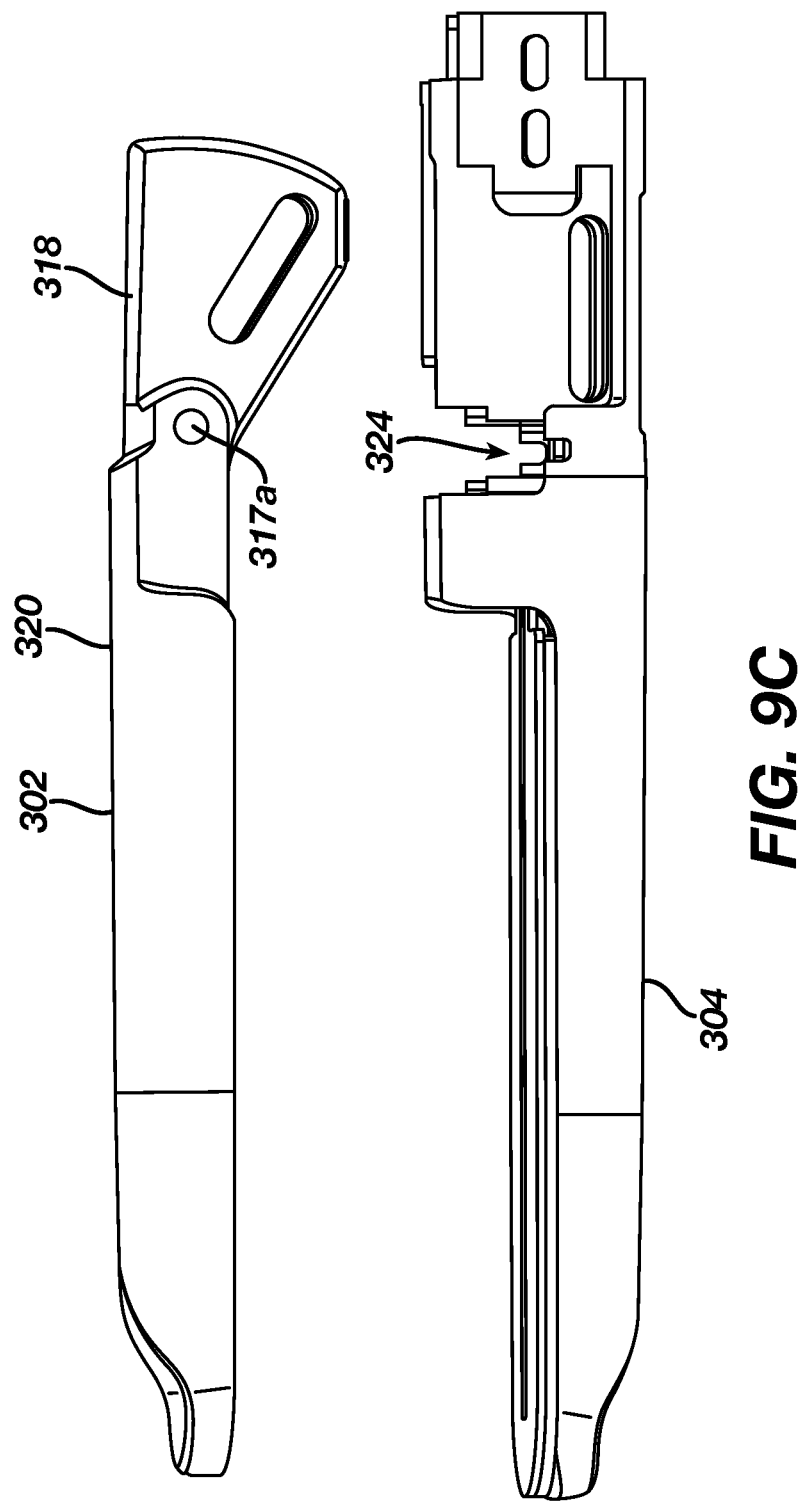
FIG. 9C is another perspective exploded view of a portion of the end effector of FIG. 9A.

FIGS. 9A-9C illustrate that the end effector 300 can generally have a configuration similar to that of end effector 200 (FIGS. 4A-4C). Thus, the effector 300 has an upper jaw 302 and a lower jaw 304 having respective first and second tissue contacting surfaces 306, 308. The jaws 302, 304 are pivotably coupled to each other at a pivot joint 312. In this embodiment, the lower jaw 304 is a stationary jaw whereas the upper jaw 302 is a movable jaw that is configured to pivot relative to the lower jaw 304. In other embodiments, both jaws can pivot about the pivot joint. One or both of the jaws 302, 304 can include electrodes 310.

As shown in FIGS. 9A and 9B, the effector 300 includes an arcuate cover 316 disposed at a proximal portion thereof, which can have any suitable configuration. As also shown, the effector 300 includes first and second connecting members 314a, 314b disposed on opposite sides (e.g., on the left and right sides) of the lower jaw 304 within respective slots 324a, 324b. Each of the first and second connecting members 314a, 314b can be fixed within the slot in one of multiple positions so as to position the first and second tissue contacting surfaces 306, 308 of the upper and lower jaws 302, 304 at a predetermined distance (or gap) from one another when the upper and lower jaws 302, 304 jaws are in the closed position. The connecting members 314a, 314b can be substantially identical and therefore it will be understood that features discussed with respect to only one of the connecting members can apply equally to the other connecting member. In this embodiment, a bridge portion 319 extends between and is connected to the connecting members 314a, 314b. The bridge portion can facilitate handling of the connecting members and/or adjustment of the connecting members within the slots.

Figure 10:
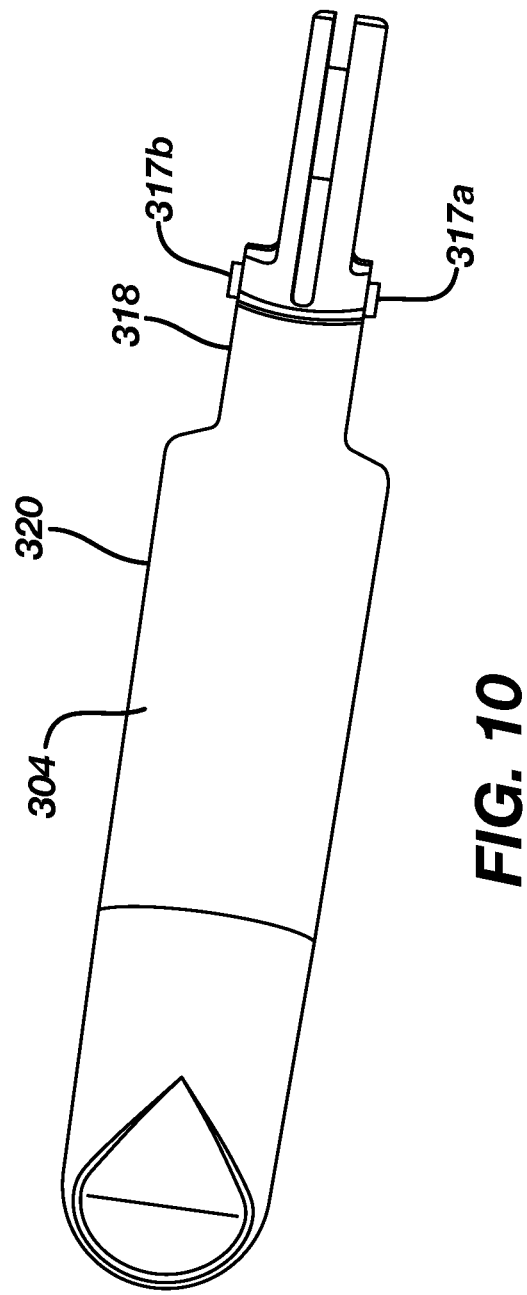
FIG. 10 is a top view of an upper jaw of the end effector of FIG. 9A.

As shown in FIGS. 9A-9C and 10, the upper jaw 304 has a proximal portion 318 and a distal portion 320 having the tissue contacting surface 306. In the illustrated embodiment, the upper jaw 302 has first and second pins 317a, 317b extending laterally from both sides (e.g., left and right) of the upper jaw 302, as also shown in FIG. 10. The first and second pins 317a, 317b can be similar or substantially identical to one another and they are configured to be inserted into respective bores formed in the connecting members 314a, 314b, as discussed in more detail below. The first and second pins 317a, 317b can be coupled to the upper jaw 302 using any suitable technique or they can be integrally and/or monolithically formed with the upper jaw 302.

The lower jaw 304 can have any suitable configuration. As mentioned above, the lower jaw 304 has first and second slots 324a, 324b in opposite walls thereof for receiving the first and second connecting members 314a, 314b therein. The first and second slots 324a, 324b can have any suitable configuration. In the illustrated embodiment, the first and second slots 324a, 324b are similar to slots 224a, 224b (FIGS. 4B, 8C, and 8D) and have a configuration corresponding to a configuration of connecting members 314a, 314b. However, the slots 324a, 324b can also have other features configured to facilitate coupling to the connecting members and at least a portion of the bridge portion 319, as discussed in more detail below. The first and second slots 324a, 324b are formed in the lower jaw 304 such that each of the first and second mating pins 317a, 317b formed on the upper jaw 302 faces a respective slot and is received within a bore of one of the connecting members 314a, 314b.

Figure 13A:
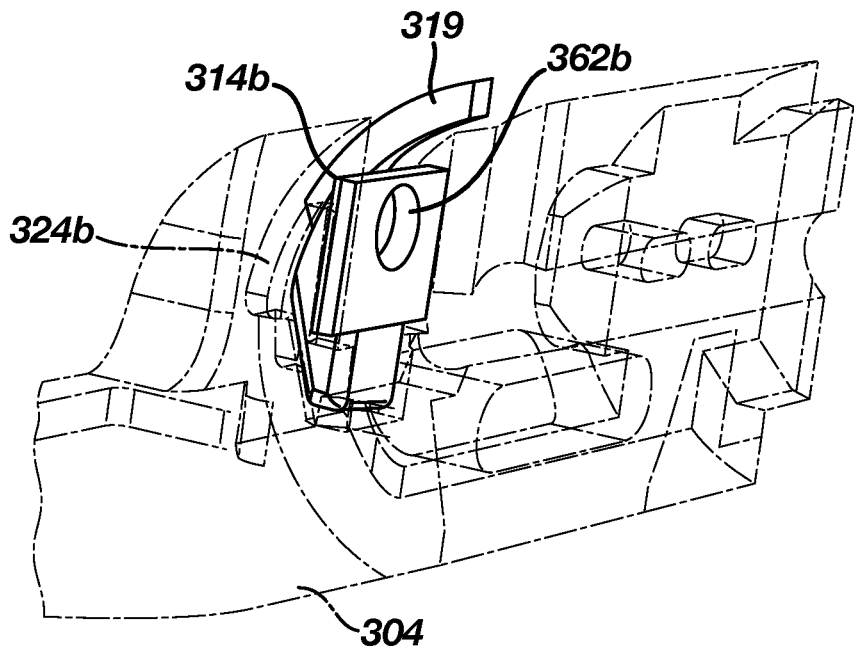
FIG. 13A is a perspective partially transparent cross-sectional top view of a lower jaw of the end effector of FIG. 9A, showing one of the connecting members seated in a slot formed in the lower jaw.
Figure 13B:
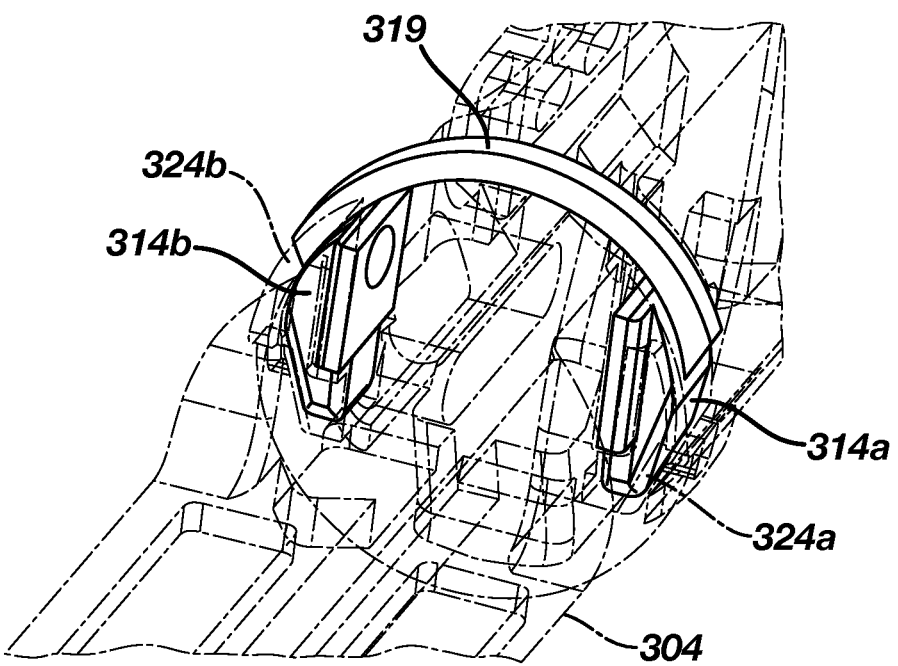
FIG. 13B is another perspective partially transparent cross-sectional view of a lower jaw of the end effector of FIG. 9A, showing both connecting members seated in opposed slots formed in the lower jaw.

As shown in FIG. 9A and further shown in FIG. 13B, an arcuate bridge portion 319 extends between the connecting members 314a, 314b and extends along a top surface of the upper jaw. While certain figures illustrate the bridge as having two halves, one connected to each connecting member 314a, 314b, the bridge 319 is preferably a single unitary member that connects the two connecting members 314a, 314b. The first and second connecting members 314a, 314b can have any suitable configuration. In the illustrated embodiment, each connecting member 314a, 314b has a body 360 and the arcuate bridge portion 319 extends therefrom.

Figure 11C:
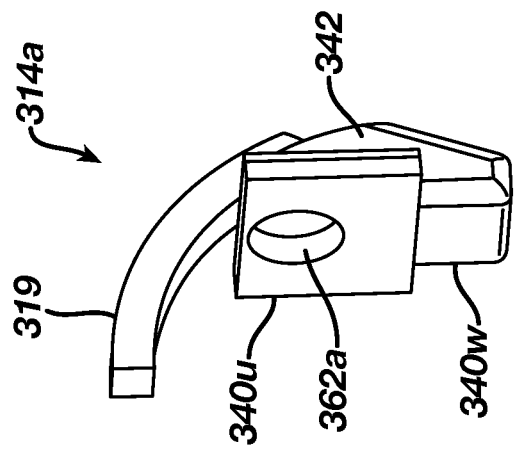
FIG. 11C is another perspective view of the connecting member of FIG. 9A.
Figure 11B:
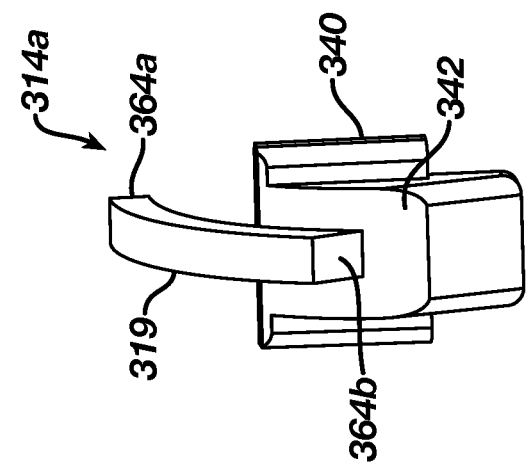
FIG. 11B is another perspective view of the connecting member of FIG. 9A.
Figure 11A:
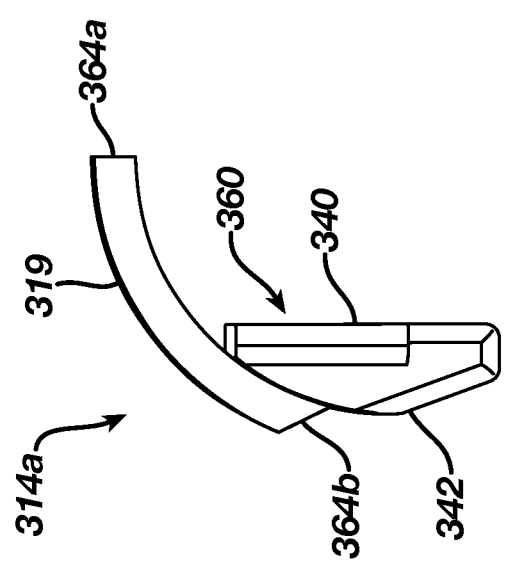
FIG. 11A is a perspective view of a connecting member of the end effector of FIG. 9A.
Figure 12:
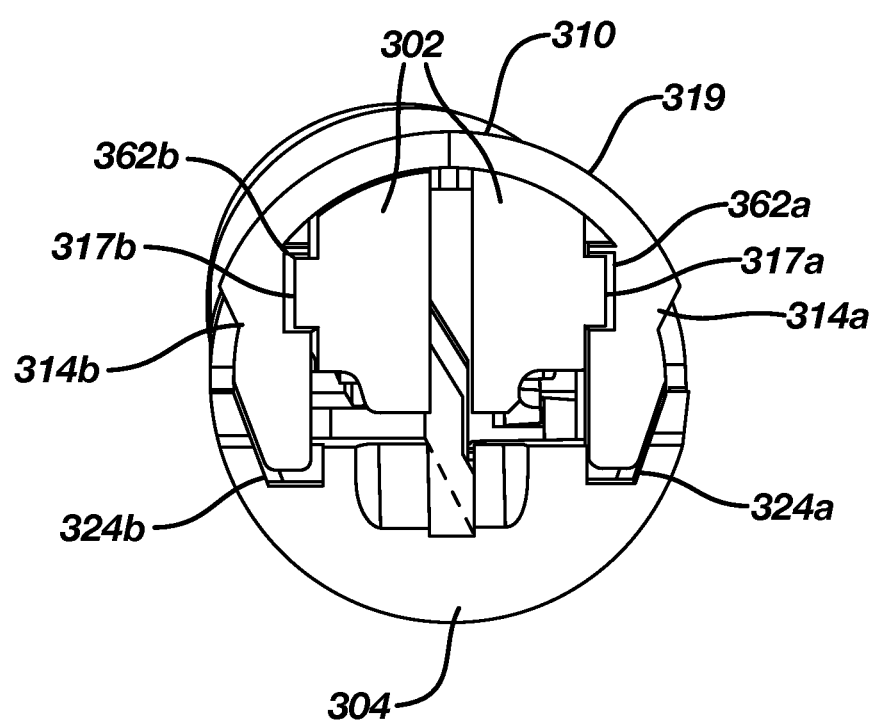
FIG. 12 is a cross-sectional end view taken across line 12-12 of the end effector of FIG. 9A.

FIGS. 11A-11C illustrate different views of connecting member 314a, and it will be understood that connecting member 314b can have the same configuration. A body 360 the connecting member 314a is generally similar to connecting member 214a (FIGS. 6A-6C). Thus, as shown, the connecting member 314a has a generally T-shaped front wall 340 having upper and lower portions 340u, 340w, and a generally convex back wall 342 shaped similarly to back wall 242 of connecting member 214a (FIGS. 6A and 6C). The connecting member 314a further has a bore 362a in the front wall 340 thereof extending at least partially through the body 360. As shown in FIG. 11C, the bore 362a can be formed approximately mid-way between the left and right sides of the front wall 340. The bore 362a can be a blind bore and it can be configured to fit therein at least a portion of the pin 317a extending from the upper jaw 302, as shown in FIG. 12. Thus, a shape and a size of the bore 362a can correspond to those of the pin 317a.

The elongate bridge portion 319 (only half of which is shown) can have an upper end 364a and a lower end 364b and it can extend from the back wall 342 of the connecting member 314a and arch beyond the body 360, as shown in FIGS. 11A-11C. The bridge portion 319 can be coupled to or integrally and/or monolithically formed with the body 360 of the connecting member so as to extend from a portion of the back wall 342 that is approximately in mid-way between the left and right sides of the connecting member 314a. The bridge portion 319 can have a generally rectangular or square cross-section. However, one skilled in the art will appreciate that it can have any other cross-sectional shape (e.g., rounded, oval, etc.).

As shown, a surface of the lower end 364b of the bridge portion 319 can be slanted toward the surface of the back wall 342. The surface of the lower end 364b can seat against an inner surface of a respective one of the slots 324a, 324b in the lower jaw 302 that is configured accordingly, as shown in FIGS. 12, 13A, and 13B. As also shown, a surface of the upper end 364a of the bridge portion 319 can be substantially planar.

The connecting members 314a, 314b and the bridge portion 319 can be formed as separate components or as a single unitary, monolithic member in any suitable manner. For example, the components can be made using injection molding (e.g., metal injection molding) from stainless steel. However, one skilled in the art will understand that the connecting members and the bridge portion can be manufactured using any suitable process, from any suitable materials.

Regardless of how the connecting members and the bridge extending therebetween are manufactured, such a configuration will improve the strength of the lower jaw. After being fixed into position, the bridge completes a 360° structure providing hoop strength to the lower jaw. Such an arrangement can be beneficial for strengthening the lower jaw. For example, when the jaws are approximated to grasp and compress tissue therebetween, forces exerted on the lower jaw may force the pivoting of the connecting members 314a, 314b laterally from the axis of the surgical device shaft. The bridge will counteract such forces to thus prevent movement and deformation of the lower jaw.

Figure 5B:
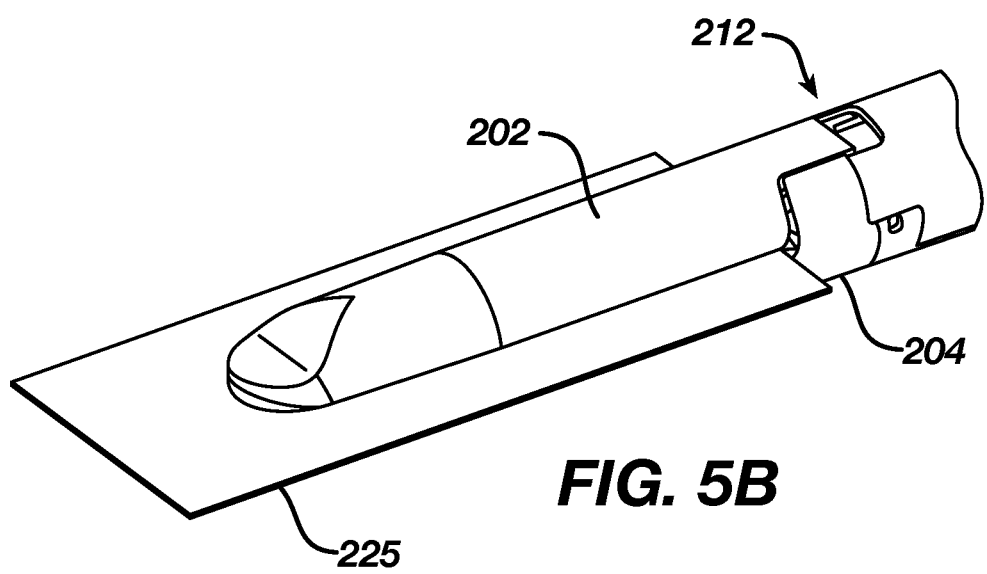
FIG. 5B is a perspective view of the end effector of FIG. 4A, showing one embodiment of a shim positioned between the jaws.

As shown in FIG. 12, the upper and lower jaws 302, 304 can be aligned with respect to one another such that the pins 317a, 317b extending from opposite sides of the upper jaw 304 are inserted into the bores 362a, 362b, respectively, formed in the connecting members 314a, 314b that are, in turn, fixedly seated within the slots 324a, 324b, respectively, formed in opposite sides of the lower jaw 302. In this way, the upper and lower jaws 302, 304 are pivotably connected to one another, and in particular the upper jaw 302 can pivot about the pins 317a, 317b. A distance between tissue contacting surfaces 306, 308 of the upper and lower jaws 302, 304 is adjusted by sliding each connecting member 314a, 314b in their respective slot, as previously described above. Once a desired tissue gap is achieved, the connecting members can be fixed, temporarily or permanently, with the slots. The position of the connecting members within the slots can be adjusted using a shim, spacer, or other feature that allows the connecting member to be disposed in a specific position within the slot. For example, in one embodiment, a spacer or shim can be positioned between the upper and lower jaws 302, 304, and, with the jaws 302, 304 in the closed position the connecting members 314a, 314b can be fixed within the slots 324a, 324b. For example, a spacer can be positioned between the upper and lower jaws 302, 304 in the closed position similar to spacer 225 (FIG. 5B). Any other suitable feature(s) and/or techniques can be used to adjust a position of the connecting members 314a, 314b within the slots 324a, 324b. In addition, in some embodiments, a technique used can be such that no shim or spacer can be required.

In some embodiments, the connecting member can be fixed to one of the jaws such that first and second tissue contacting surfaces of the upper and lower jaws are aligned so that they are approximately parallel to one another in the closed position. However, in other embodiments, the connecting member can be fixed to one of the jaws such that the first and second tissue contacting surfaces are oriented in different ways with respect to each other. For example, they can be positioned at an angle with respect to one another in the closed position. In this way, different portions of the tissue contacting surfaces can engage tissue in different manner. For example, one longitudinal side of the tissue contacting surfaces can engage the tissue before the other longitudinal side. As another variation, the second tissue contacting surfaces can be fixed in an orientation such that their distal ends engage the tissue prior to the tissue being engaged with the rest of the surface area, or vice versa.

In conventional end effectors, both lower and upper jaws can have openings formed therein that receive pins for pivotably coupling the jaws to each other. In contrast, in the illustrated embodiments, the lower jaw (e.g., lower jaw 204 or 304) may not have such openings formed therein and rather has first and second slots (e.g., slots 224a, 224b or 324a, 324b) configured to receive first and second connecting members (e.g., connecting members 214a, 214b or 314a, 314b). Thus, while the conventional design requires aligning multiple openings (e.g., four openings) formed in each of the jaws with respective pins (e.g., four pins), which can make it challenging to properly control alignment of all the elements, the embodiments described herein allow for a simpler, more effective and reliable method of assembly of the end effector such that a gap between the jaws is adjusted with a desired tolerance.

A person skilled in the art will appreciate that, while not described in detail herein, the jaws can include other features to facilitate opening and closing of the jaws. For example, the upper jaw can include a slot formed therein and the elongate shaft can be configured to slide distally relative to the jaws to cause a pin disposed within the slot to force the upper jaw to move to a closed position. Other closure techniques known in the art can also be used, and the connecting member disclosed herein is not intended to be limited to use with the illustrated jaws.

As indicated above, during manufacturing the connecting members can be fixed, temporarily or permanently, with the slots using various techniques. The connecting members can be fixed within the slots by, for example, welding (e.g., laser welding) which can involve weld the material forming the lower jaw and/or the material forming the connecting member together. Alternatively, additional weld material can be utilized. As another non-limiting example, the connecting members can be fixed within the slots by application of an adhesive, thermoset or thermoplastic overmold, or any other suitable technique(s).

A person skilled in the art will appreciate that the techniques described herein have application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical end effector, comprising:
    first and second jaws pivotally coupled to one another, each jaw having a tissue contacting surface, and the first and second jaws being movable between an open position in which the tissue contacting surfaces are spaced apart and a closed position in which the tissue contacting surfaces are configured to engage tissue therebetween;
    a connecting member pivotally coupled to the first jaw and disposed within a slot formed in the second jaw, the slot having a plurality of positions for seating the connecting member such that a gap between the tissue contacting surfaces exists when the first and second jaws are in the closed position, each of the plurality of positions corresponding to a different size of the gap, and the connecting member being immovably and permanently fixed within the slot at one of the plurality of positions, the connecting member allowing pivotal movement of the jaws between the open and closed positions.

2. The surgical end effector of claim 1, wherein the connecting member includes a pin formed thereon that extends into a bore formed in the first jaw.

3. The surgical end effector of claim 1, wherein, prior to being fixed to the second jaw, the connecting member is configured to slide within the slot in a direction substantially perpendicular to a longitudinal axis of the first and second jaws.

4. The surgical end effector of claim 1, wherein the slot comprises a first slot, the surgical end effector further comprises a second slot, and the first and second slots are formed in opposite sides of the second jaw.

5. The surgical end effector of claim 1, wherein the second jaw is a stationary jaw and the first jaw is a movable jaw that is configured to pivot relative to the second jaw.

6. A surgical end effector, comprising:
    first and second jaws pivotally coupled to one another, each jaw having a tissue contacting surface, and the first and second jaws being movable between an open position in which the tissue contacting surfaces are spaced apart and a closed position in which the tissue contacting surfaces are configured to engage tissue therebetween, the first jaw having a bore formed therein and the second jaw having an elongated slot formed therein, the elongated slot having a groove formed therein; and
    a connecting member disposed within the elongated slot of the second jaw and having a pin formed thereon and extending into the bore of the first jaw, the connecting member being immovably and permanently fixed within the elongated slot at one of a plurality of positions within the elongated slot that maintains a predetermined gap between the tissue contacting surfaces of the first and second jaws when the first and second jaws are in the closed position, each of the plurality of positions corresponding to a different size of the gap, the connecting member including a tongue disposed at least partially in the groove.

7. The surgical end effector of claim 6, wherein the pin is rotatably disposed within the bore to allow pivotal movement between the first and second jaws.

8. The surgical end effector of claim 6, wherein the elongated slot has a length that is greater than a height of the connecting member.

9. The surgical end effector of claim 6, wherein the elongated slot extends in a direction substantially perpendicular to a longitudinal axis of the first and second jaws.

10. The surgical end effector of claim 6, wherein the connecting member comprises a first connecting member and the elongated slot comprises a first slot, and the surgical end effector further includes a second connecting member and a second slot.

11. The surgical end effector of claim 10, wherein the first and second slots are formed in opposite sides of the second jaw.

12. The surgical end effector of claim 6, wherein the second jaw is a stationary jaw and the first jaw is a movable jaw that is pivotable relative to the second jaw.

13. A surgical end effector, comprising:
first and second jaws pivotally coupled to one another, each jaw having a tissue contacting surface, and the first and second jaws being movable between an open position in which the tissue contacting surfaces are spaced apart and a closed position in which the tissue contacting surfaces are configured to engage tissue therebetween, the second jaw having an elongated slot formed therein; and
a connecting member disposed at least partially within the elongated slot of the second jaw, the connecting member being immovably and permanently fixed within the elongated slot at one of a plurality of positions within the elongated slot that maintains a predetermined gap between the tissue contacting surfaces of the first and second jaws when the first and second jaws are in the closed position, each of the plurality of positions corresponding to a different size of the gap, the connecting member including a first mating portion positioned in the elongated slot and a second mating portion oriented orthogonal to the first mating portion and inserted into a bore formed in the first jaw.

14. The surgical end effector of claim 13, wherein the second mating portion comprises a pin disposed proximate a first end of the first mating portion.

15. The surgical end effector of claim 13, wherein the first mating portion includes a front wall having a front upper portion and a front lower portion, the upper portion having a width greater than a width of the lower portion.

16. The surgical end effector of claim 15, wherein the first mating portion includes a back wall, the back wall having a back upper portion extending outwardly away from the front wall in an upper-to-lower direction, and a back lower portion extending toward the front wall in the upper-to-lower direction.

17. The surgical end effector of claim 16, wherein the first mating portion includes a mid-portion disposed between the back upper portion and the back lower portion.

18. The surgical end effector of claim 17, wherein the mid-portion comprises an edge.

19. The surgical end effector of claim 17, wherein the mid-portion is disposed closer to a lower end of the first mating portion than an upper end of the first mating portion, the lower end being opposite the upper end.

20. The surgical end effector of claim 16, wherein the back upper portion is convexly shaped.

* * * * *